(12) United States Patent
Allegra et al.

(10) Patent No.: US 11,903,695 B2
(45) Date of Patent: Feb. 20, 2024

(54) SENSOR DEVICES AND SYSTEMS FOR MONITORING MARKERS IN BREATH

(71) Applicant: BIOLUM SCIENCES LLC, Houston, TX (US)

(72) Inventors: Edward C. Allegra, Dallas, TX (US); Miguel E. Quimbar, Dallas, TX (US); Jack P. Reynolds, Dallas, TX (US)

(73) Assignee: Biolum Sciences LLC, Houston, TX (US)

( * ) Notice: Subject to any disclaimer, the term of this patent is extended or adjusted under 35 U.S.C. 154(b) by 828 days.

(21) Appl. No.: 16/981,237

(22) PCT Filed: Mar. 13, 2019

(86) PCT No.: PCT/US2019/022076
§ 371 (c)(1),
(2) Date: Sep. 15, 2020

(87) PCT Pub. No.: WO2019/178247
PCT Pub. Date: Sep. 19, 2019

(65) Prior Publication Data
US 2021/0059560 A1 Mar. 4, 2021

Related U.S. Application Data

(60) Provisional application No. 62/643,442, filed on Mar. 15, 2018.

(51) Int. Cl.
*A61B 5/08* (2006.01)
*A61B 5/09* (2006.01)
(Continued)

(52) U.S. Cl.
CPC .............. *A61B 5/082* (2013.01); *A61B 5/097* (2013.01); *A61B 5/4839* (2013.01); *A61B 10/00* (2013.01);
(Continued)

(58) Field of Classification Search
CPC ....... A61B 5/082; A61B 5/097; A61B 5/4839; A61B 10/00; A61B 2010/0087; G01N 33/497
(Continued)

(56) References Cited

U.S. PATENT DOCUMENTS 3,393,053 A * 7/1968 Jones ....................... G01N 7/04
422/92
6,467,333 B2 10/2002 Lewis et al.
(Continued)

FOREIGN PATENT DOCUMENTS

| WO | WO-9731261 A1 * | 8/1997 | ........... G01N 21/783 |
| WO | WO-03040719 A1 * | 5/2003 | ........... G01N 33/497 |
| WO | WO-2004065404 A1 * | 8/2004 | ............. B82Y 30/00 |

OTHER PUBLICATIONS

International Search Report and Written Opinion dated Jun. 21, 2019 in PCT Application No. PCT/US2019/022076.

*Primary Examiner* — Arlen Soderquist
(74) *Attorney, Agent, or Firm* — McDermott Will and Emery LLP

(57) ABSTRACT

The disclosure relates to devices, systems and methods for detecting markers in breath, more specifically volatile and non-volatile markers associated with pulmonary diseases such as, for example, asthma, chronic obstructive pulmonary disease (COPD), or cystic fibrosis (CF), in exhaled breath condensate (EBC).

53 Claims, 17 Drawing Sheets

(51) Int. Cl.
*A61B 10/00* (2006.01)
*G01N 33/497* (2006.01)
*A61B 5/097* (2006.01)
*A61B 5/00* (2006.01)

(52) U.S. Cl.
CPC .... *A61B 2010/0087* (2013.01); *G01N 33/497* (2013.01)

(58) Field of Classification Search
USPC ...................................... 422/83–84; 436/181
See application file for complete search history.

(56) References Cited

U.S. PATENT DOCUMENTS

| | | |
|---|---|---|
| 8,394,030 B2 | 3/2013 | Varga et al. |
| 9,643,186 B1 | 5/2017 | Ahmad et al. |
| 2003/0023389 A1* | 1/2003 | Rothe ................. G01N 33/497 702/23 |
| 2004/0138577 A1 | 7/2004 | Kline |
| 2005/0065446 A1 | 3/2005 | Talton |
| 2005/0233459 A1* | 10/2005 | Melker ................ G01N 33/497 436/56 |
| 2007/0073183 A1 | 3/2007 | Kline |
| 2010/0324439 A1 | 12/2010 | Davenport |
| 2014/0276100 A1 | 9/2014 | Satterfield et al. |
| 2016/0022946 A1* | 1/2016 | Sislian ................ A61M 16/105 600/543 |
| 2017/0065208 A1 | 3/2017 | Furusaki et al. |

\* cited by examiner

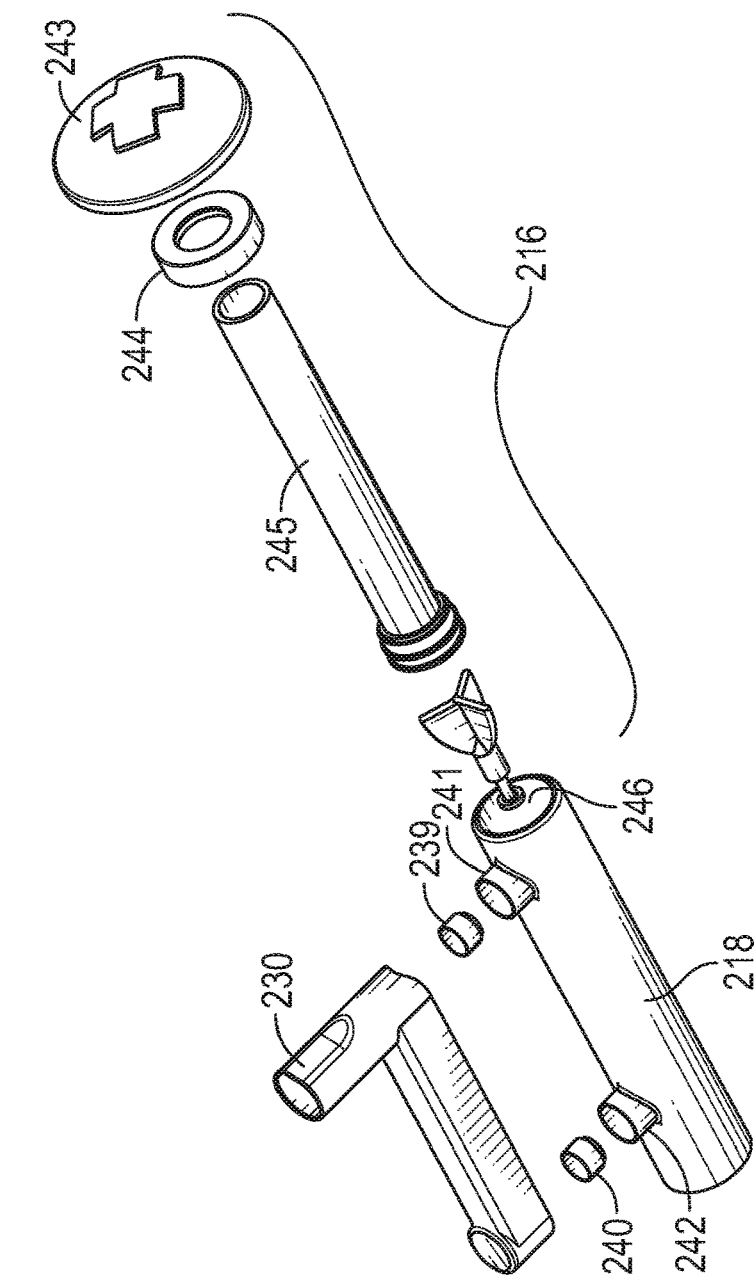
FIG. 2E-2
FIG. 2E
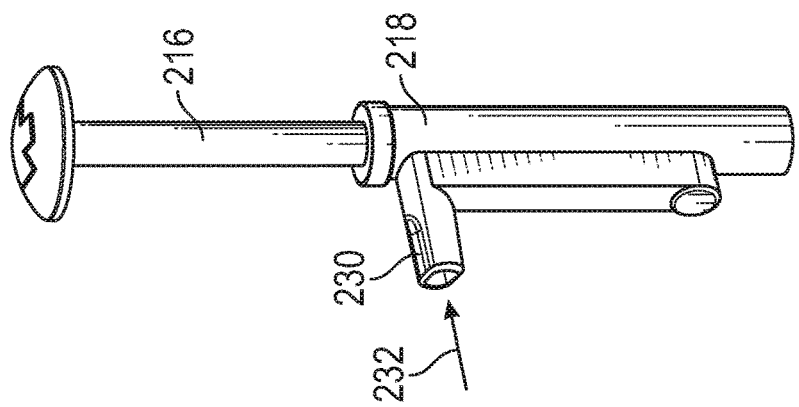
FIG. 2E-1

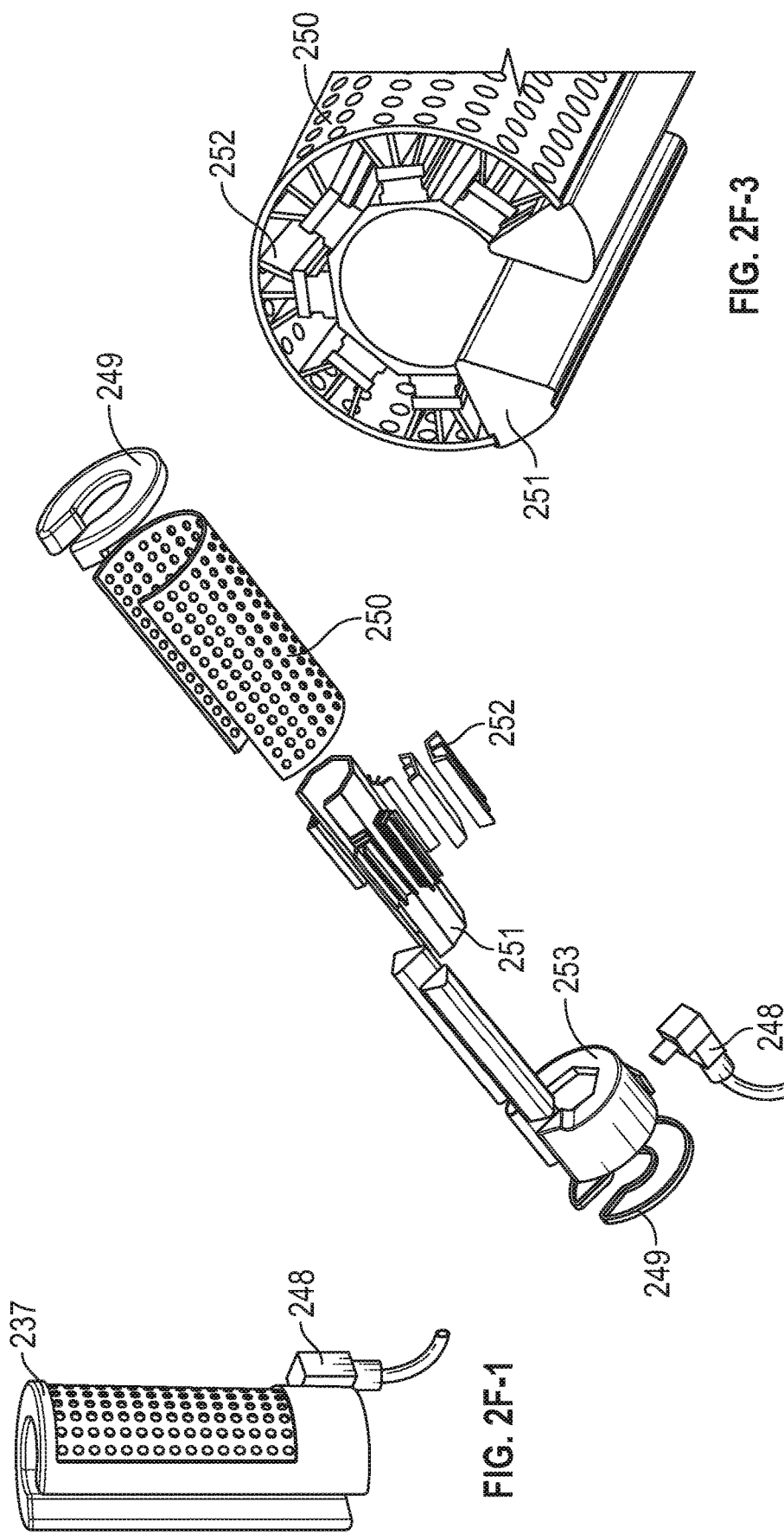

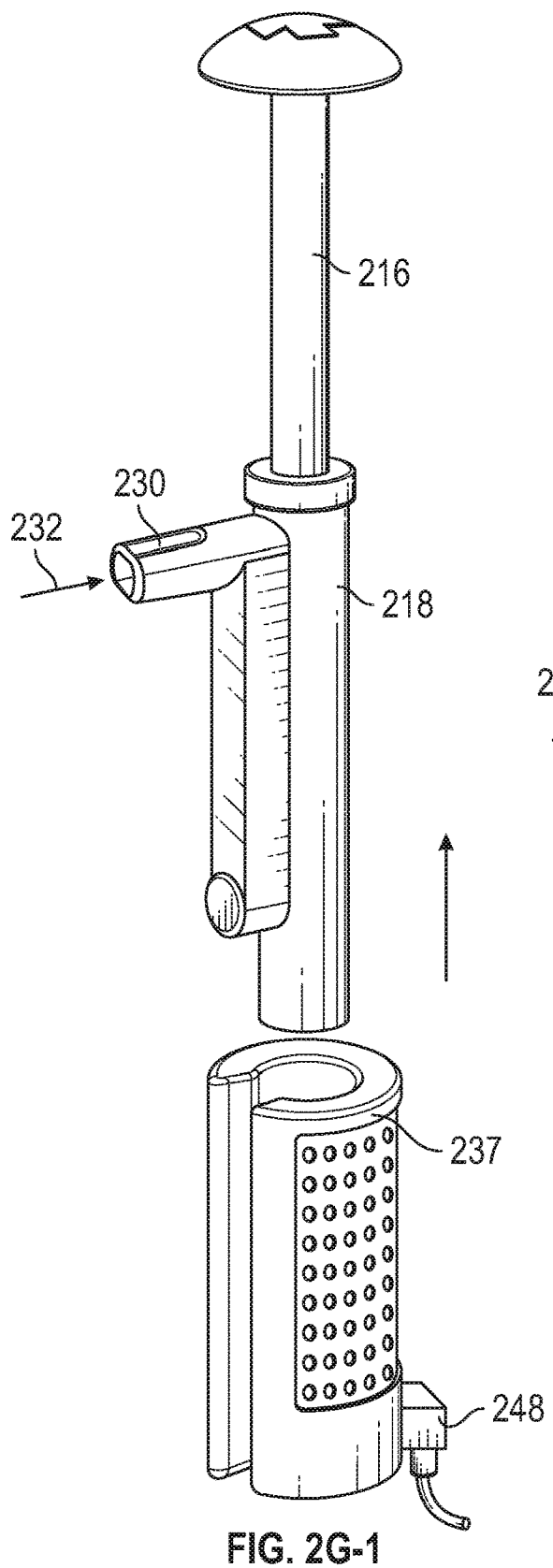
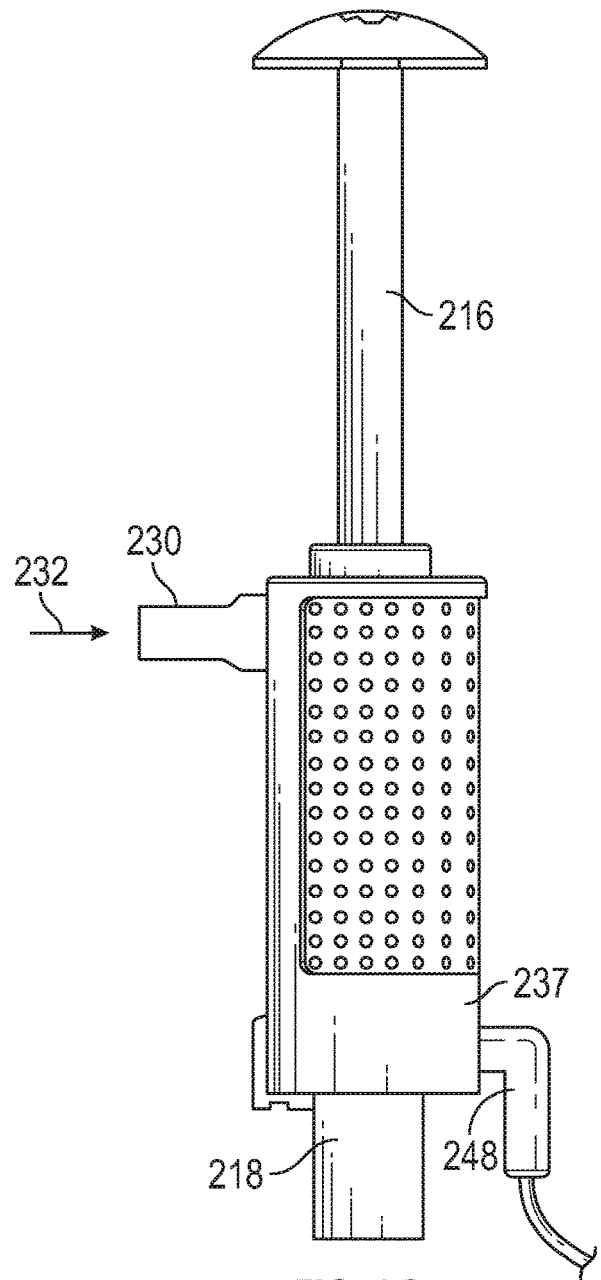
FIG. 2G-1
FIG. 2G-2
FIG. 2G

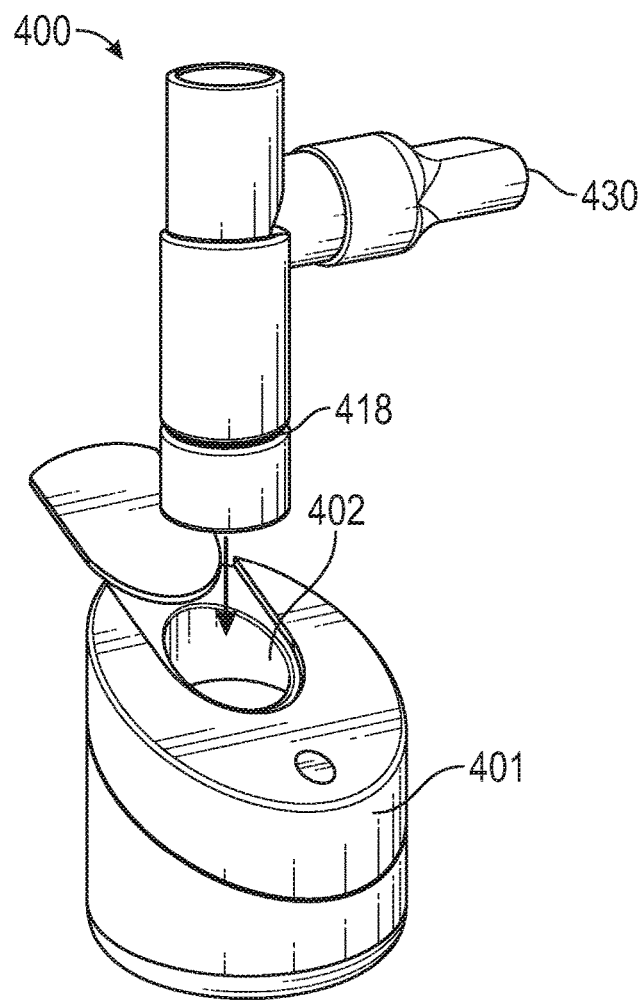
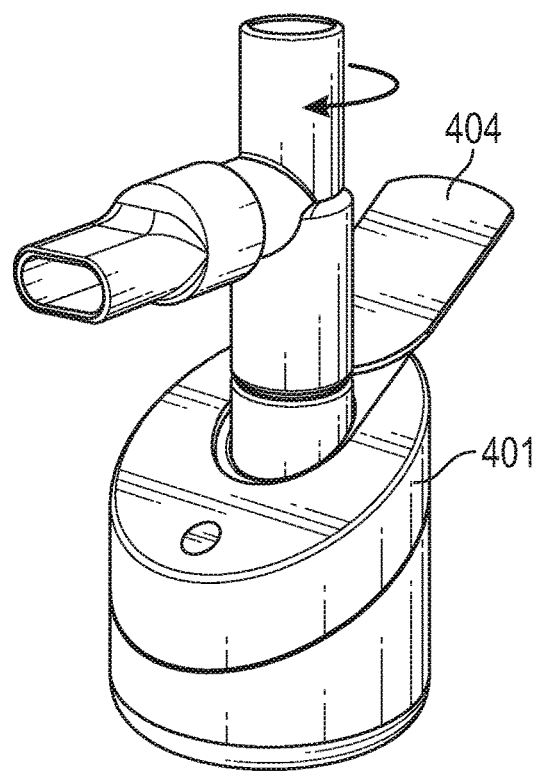
FIG. 4A
FIG. 4B

SENSOR DEVICES AND SYSTEMS FOR MONITORING MARKERS IN BREATH

CROSS-REFERENCE TO RELATED APPLICATIONS

The present application is a United States National Phase under 35 U.S.C. § 371 of International Application No. PCT/US2019/022076, filed on Mar. 13, 2019, which claims the benefit of, and priority to, U.S. Prov. No. 62/643,442, filed on Mar. 15, 2018, the entire contents of both of which are incorporated herein by reference for all purposes.

TECHNICAL FIELD

The present disclosure generally relates to articles and system for monitoring markers in exhaled breath condensate (EBC). In particular, the disclosure provides a multi-chambered article, wherein the probes that are specific for the marker are kept separate from the vehicle 104 and the detection system until a sample containing the EBC is received and the test is initiated by allowing the probes to mix with the vehicle 104 and react with the marker. The reaction between the probe 110 and the marker generates a signal, which is detected in situ and optionally processed by the detection system to provide a user with readout of the parameter being measured, e.g., levels, concentration, or amount of the marker in the sample.

BACKGROUND

Exhaled breath condensate (EBC) contains every species that the airway lining fluid contains, but in very small concentrations. Molecules such as hydrogen ions ($H^+$), hydrogen peroxide ($H_2O_2$), malondialdehyde, 8-isoprostanes, thiobarbituric acid reactive substances (TBARS), nitrosothiols, and nitric oxide-derived products (e.g., nitrite/nitrate) in EBC are thought to serve as markers for human diseases (Lee et al., *Clin Transl Sci.*, 2(2):150-5, 2009; Liu et al., *Respiration*, 74(6):617-23, 2007). With improved detection systems and methods, these markers have been utilized, with some success, in the diagnosis of pulmonary diseases such as asthma (Teng et al., *Chest*, 140, 108-116, 2011), chronic obstructive pulmonary disease (Murata et al., *COPD* 11, 81-87, 2014), cystic fibrosis (Zang et al., *J Proteome Res.*, 16(2):550-558, 2017), bronchiectasis (Nagaraja et al., *Lung India*, 29(2), 123-127, 2012), and lung cancer (Chan et al., *J Thorac Oncol.*, 4(2):172-8, 2009). In addition, volatile organic compounds (VOC) in exhaled breath, e.g., carbon monoxide, nitric oxide, alkanes and benzene derivatives (Pauling et al., *Proc Natl Acad Sci USA*, 68:2374-6, 1971; Gordon et al., *Clin Chem* 31:1278-82, 1985) were identified as markers for lung diseases (Kharitonov et al., *Chest* 130:1541-6, 2006; Koutsokera et al., *Curr Med Chem*, 15:620-30, 2008) and more specifically lung cancer (Poli et al., *Respir Res* 6:71, 2005; Phillips et al., *Cancer Biomark* 3:95-109, 2007; Poli et al., *Acta Biomed* 79 Suppl 1:64-72, 2008).

A variety of systems and devices have been used to detect EBC markers, including, luminescent or fluorescent detection (Zappacosta et al., *Clin. Chim. Acta*, 310, 187-191, 2001), electrochemistry (Chen et al., *Analyst* 137 (2012) 49-58), and chromatography (Harshman et al., *Chromatography*, 1(3), 108-119, 2014). More sophisticated techniques such as mass spectrometry and magnetic resonance (NMR) have also been employed (Kelly et al., *Chest*, 151(2):262-277, 2017; Lippert et al., *J. Am. Chem. Soc.* 133, 3776-3779, 2011). While these systems and devices are reliable, they require specialized systems and personnel for operation. Moreover, these instruments are not automated, are tedious, expensive, and also time consuming to operate.

One of the most well recognized markers of pulmonary diseases, such as asthma and COPD, is hydrogen peroxide ($H_2O_2$). See, Kostikas et al., *Chest*, 124(4):1373-1380, 2003; Nowak et al., *Respiratory Medicine*, 93(6):389-396, 1999; Teng et al., *Chest*, 140(1):108-116, 2011; and Antczak et al., *Eur Respir J*, 10:1231-1241, 1997). $H_2O_2$ is a protonated form of superoxide ($O_2^{2-}$) and is produced in biological systems by the dismutation of superoxide anion in a reaction carried out by the enzyme superoxide dismutase (SOD) (Manda et al., *Current Chemical Biology*, 3(1), 22-46, 2009). $H_2O_2$ production is exacerbated in patients with pulmonary diseases (Dekhuijzen et al., *AJRCCR*, 154 (3):813-816, 1996). Two clinical trials are currently examining EBC peroxide levels as a marker of pulmonary diseases. See, National Clinical Trials ID No. NCT03055923 entitled "Exhaled hydrogen peroxide as a marker of lung disease" and NCT01402297 entitled "Hydrogen Peroxide and Nitrite Reduction in Exhaled Breath Condensate of COPD Patients." A secondary EBC marker, such as malondialdehyde (Gong et al., *J Expo Sci Environ Epidemiol.*, 23(3): 322-327, 2013) 8-isoprostane, TBARS, nitrotyrosine, nitrosothiols nitrite/nitrate, including, biomolecules such as leukotrienes, PGE2, and cytokines, may also be indicative of pulmonary diseases (Antczak et al., *IJOMEH*, 15 (4), 317-323, 2002).

Although EBC peroxide levels can be used to assess alterations in alveolar fluid that are considered to be more specific indicators of oxidative lung damage, it is not without drawbacks. In an exhaled breath sample, hydrogen peroxide will generally be present in the liquid phase, but it may also be present in the gas phase of the breath. Thus, the detection systems may be compatible with both gas phase and liquid phase. Additionally, hydrogen peroxide contents in exhaled air are low and other gases, e.g., $CO_2$ at about 5% volume, $O_2$ at about 18% volume and $N_2$ at about 75% volume, may limit accurate measurements of the relatively low hydrogen peroxide contents in the EBC. Presently, $H_2O_2$ in EBC is detected using conventional electrochemical and chemical detection systems, wherein the capturing and detecting (of $H_2O_2$) steps are both temporally and spatially discrete. For example, Senzair B. V., Enschede, Netherlands manufactures electromechanical devices for $H_2O_2$ detection in EBC, comprising the amperometric sensor and control and measurement electronics. As described in U.S. Pub. No. 2014-0021065 (to Senzair), the device electrochemically converts the hydrogen peroxide in the gaseous mixture at a sensing element of an electrochemical sensor in direct contact with the capturing means, and measuring the potential of the sensing element and/or the current through it as a result of a changing hydrogen peroxide concentration in the gaseous mixture. Measurement of $H_2O_2$ is performed with a device suitable for the on-line measurement, i.e., a computer.

To date, there does not appear to be a strong push to utilize sensors for breath condensate analysis, which may be due to lack of a direct interface between the collection unit and the measurement unit. Many of the known EBC collection units do not address a means for efficient handling and transfer of condensate to the analytical system, requiring manual extract action and preparation of samples. By using sensors that could potentially be directly integrated into the EBC collection device, the need to sample for a long time can be obviated and allow collection of samples with finer time resolution.

Accordingly, there is an unmet need for sensitive, optimized, non-invasive analytical devices that are small in size, ideally hand-held or portable or field-deployable, which can be used with precision at the point-of-care (POC) for the detection of EBC markers associated with pulmonary diseases, such as $H_2O_2$.

SUMMARY

In one embodiment, the disclosure provides an article for measuring a disease marker in exhaled breath condensate (EBC) comprising, (a) a vehicle chamber 102 containing a vehicle 104 for a probe 110; (b) an auxiliary chamber that is physically separated from the vehicle chamber 102 via a first separator 108, wherein the auxiliary chamber contains the probe 110 that is specific to the marker; (c) a reaction chamber that is physically separated from the vehicle chamber 102 or the auxiliary chamber or both the reaction chamber 120 and the auxiliary chamber via a second separator 122, wherein the reaction chamber 120 contains a surface 124 for detection of the interaction between the probe 110 and the marker. The article may comprise a plurality of plungers, the initiation of which dispenses the contents of a first chamber into a second chamber. Particularly, the article comprises a first plunger 112 which disengages the first separator 108, thereby dispensing the vehicle 104 in the vehicle chamber 102 into the auxiliary chamber to dissolve the probe 110 contained therein. The article may also comprise a second plunger 116 which disengages the second separator 122, thereby dispensing the probe 110 solution into the reaction chamber 120. The separators may comprise breakable material such as a foil or plastic or a valve system that may be disengaged, e.g., mechanically.

In some embodiments of the article of the disclosure, the auxiliary chamber contains a probe 110 composition comprising a marker-reactive chemical (C) and a dye (D). Particularly, the dye is activated by a product of the reaction between the marker and the marker-reactive chemical and the activation is initiated in situ or at the site of the reaction chamber 120. Particularly, the marker is $H_2O_2$ and the probe 110 comprises $H_2O_2$-reactive chemical such as bis(2,4,6-trichlorophenyl) oxalate, bis(2-carbopentyloxy-3,5,6-trichlorophenyl)oxalate, oxalic acid bis [2,4,5-trichloro-6-(pentyloxycarbonyl)phenyl]ester, bis(2-nitrophenyl) oxalate, bis(2,4-dinitrophenyl) oxalate, bis(2,6-dichloro-4-nitrophenyl) oxalate, bis(2,4,6-trichlorophenyl) oxalate, bis (3-trifluoromethyl-4-nitrophenyl) oxalate, bis(2-methyl 4,6-dinitrophenyl) oxalate, bis(1,2-dimethyl-4,6-dinitrophenyl) oxalate, bis(2,4-dichlorophenyl) oxalate, bis(2,5-dinitrophenyl) oxalate, bis(2-formyl-4-nitrophenyl) oxalate, bis(pentachlorophenyl) oxalate, bis(pentalluorophenyl) oxalate, bis (1,2-dihydro-2-oxo-1-pyridyl) glyoxal, bis-N-phthalmidyl oxalate, bis(2,4,5 trichloro-6-carbopentoxyphenyl) oxalate, bis(2,4,5-trichloro-6-carbobutoxyphenyl) oxalate, bis(2,4,6-trichlorophenyl) oxalate, or phthalimido 3,6,6-trisulfo-2-naphthyl oxalate. Under this embodiment, the dye (D) may be selected from iptycene compounds, anthracenes, diphenylanthracenes, 9,10-bis(phenylethynyl) anthracene, benzanthracenes, phenanthrenes, naphthacenes, pentacenes, poly(arylene)s, poly(phenylene vinylene)s, poly(phenylene ethynylene)s, 5-amino-2,3-dihydrophthalazine-1,4-dione, 3-aminophthalhydrazide, 2,4,5-triphenylimidazole, 10,10'-dialkyl-9,9'-biacridinium salts, and 9-chlorocarbonyl-10-methylacridinium chloride. The probe 110 composition may further comprise a catalyst (K) such as imidazole. The probe 110 may also comprise polymers (P) to control reaction between the reactive component and the marker. Optionally, the probe 110 may comprise reagents for detection of secondary markers, e.g., hydrogen ions ($H^+$), malondialdehyde, 8-isoprostanes, thiobarbituric acid reactive substances (TBARS), acetone, nitrosothiols, pH, and nitric oxide-derived products.

In some embodiments of the article of the disclosure, the vehicle chamber 102 contains an organic solvent selected from the group consisting of: ethylene glycol ethers, diethyl ether, diamyl ether, diphenyl ether, anisole, tetrahydrofuran, dioxane, ethyl acetate, acetone, acetonitrile, propyl formate, amyl acetate, dimethyl phthalate, diethyl phthalate, dibutyl phthalate, dioctyl phthalate, methyl formate, triacetin, diethyl oxalate, dioctyl terphthalate, citric acid ester, methyl benzoate, ethyl benzoate, butyl benzoate, benzene, ethyl benzene, butyl benzene, toluene, xylene, chlorobenzene, o-dichlorobenzene, m-dichlorobenzene, chloroform, carbon tetrachloride, hexachloroethylene, tetrachlorotetrafluoropropane, or combinations thereof.

In some embodiments of the article of the disclosure, the reaction chamber 120 may further comprise a thin transparent or translucent window 114 that is pervious to a signal, e.g., a glass window 114 that can transmit a chemiluminescent signal. The reaction chamber 120 surface 124 may comprise an adsorptive material, e.g., a chemisorptive or a physisorptive material 128 such as sponge, charcoal, activated carbon, cellulose, lignin, or polycaprolactone (PCL). The surface 124 may also comprise a chip, e.g., a microfluidic chip. The surface 124 may further comprise an elongated member 126 e.g., pin, nail, needle, rod, or plastic tip. The reaction chamber 120 may also contain a plurality of sensors, including, circuitry for the detection of the signal In some embodiments of the articles of the disclosure, a semi-disposable reaction chamber 120 comprising a sensor, as described above, is fitted with a reagent storage chamber in a manner such that, following a test, the reaction chamber may be cleaned and the reagent storage chamber may be replaced. Such a semi-disposable unit would eliminate potential waste and also save costs associated with a fully disposable reaction chamber.

In some embodiments, the article of the disclosure is fitted with a collection unit for collecting EBC, wherein the collection unit comprises a first end that is attachable to the article at the reaction chamber 120 and a second end that contains a mouthpiece 230. The first end in the collection unit may include a mesh that is pervious to gas but semi-pervious or impervious to liquid to act as a saliva trap and prevent sample contamination. The collection unit may be tubular and optionally T-shaped, L-shaped or S-Shaped. The collection unit may include a plurality of valves for dispensing the EBC sample 232 into the article. Along with this, the collection unit may include a plurality of filters preventing outside ambient air contamination.

In some embodiments, the article of the disclosure, optionally together with the collection unit, is provided with a receptacle for analytically measuring a signal generated by the probe 110-marker interaction. In one embodiment, the receptacle comprises a detector for detecting a signal, e.g., a chemiluminescent signal, a fluorescent signal or a phosphorescent signal.

In some embodiments, the disclosure provides kits comprising, in one or more packages, (1) the article described above, wherein reaction chamber 120, the auxiliary chamber and the vehicle chamber 102 are present separately or as a unit; and (2) instructions for using the kit.

In some embodiments, the disclosure provides a system for measuring a disease marker in exhaled breath condensate (EBC) comprising, (I) an article comprising, (a) a vehicle chamber 102 containing a vehicle 104 for a probe 110 for the detection of the marker; (b) an auxiliary chamber that is physically separated from the vehicle chamber 102 via a first separator 108, wherein the auxiliary chamber contains the probe 110 that is specific to the marker; and (c) a reaction chamber 120 that is physically separated from the vehicle chamber 102 or the auxiliary chamber or both the reaction chamber 120 and the auxiliary chamber via a second separator 122, wherein the reaction chamber 120 contains a surface 124 for detection of the interaction between the probe 110 and the marker; (II) a collection unit comprising a first end that is attachable to the article and a second end that contains a mouthpiece 230; and optionally (III) a receptacle for analytically measuring a signal generated by the probe 110-marker interaction. The components of such a system may be provided in a kit together with instructions for using the kit.

In some embodiments, the disclosure provides a system for measuring a disease marker in exhaled breath condensate (EBC) comprising, (A) a collection unit comprising a collection chamber 218 which is engaged with a plunger 216 at a first end and a mixing unit 270 at a second end; (B) a mouthpiece 230 which is engaged with the collection chamber via an inlet 241 and an outlet 242, each of which optionally comprises valves 239 and 240; and (C) a cooling device 237 which is engaged with an outer surface of the collection chamber, wherein the cooling device covers a substantial portion of the collective chamber. Preferably, the mixing unit 270 comprises (a) a vehicle chamber 202 containing a vehicle 204 for a probe 210 for the detection of the marker; (b) an auxiliary chamber that is physically separated from the vehicle chamber 202 via a first separator 208, wherein the auxiliary chamber contains the probe 210 that is specific to the marker; and (c) a reaction chamber 220 that is physically separated from the vehicle chamber 202 or the auxiliary chamber 206 or both the reaction chamber 220 and the auxiliary chamber 206 via a second separator 222, wherein the reaction chamber 220 contains a surface 224 for detection of the interaction between the probe 210 and the marker. In some embodiments, the system further comprises (D) a receptacle 280 comprising a well, which is capable of engaging with the mixing unit 270 and which comprises a reader 234 and a vortex mixer 235. Preferably, the well comprises an outer surface 233 that comprises a light-shield material. The components of such a system may be provided in a kit together with instructions for using the kit.

In some embodiments, the disclosure provides a system for analyzing exhaled breath condensate (EBC) for disease markers, comprising a collection unit for collecting exhaled breath condensate (EBC) comprising (A) a collection chamber 218; and (B) a mouthpiece 230, which is engaged with the collection chamber via an inlet 241 and an outlet 242, each of which optionally comprises valves 239 and 240. Preferably, the mouthpiece 230 is detachably engaged with an outer wall of the collection chamber 218 at ports 241 and 242, each comprising valves 239 and 240. The collection chamber 218 and the mouthpiece 230 may be provided as a single unit or separate units. Additionally, the collection chamber 218 may be engaged with (C) a plunger 216 at a first end and (D) a mixing unit 270 at a second end. In some embodiments, when the plunger is engaged, the EBC is moved from a first end of the collection chamber 218 (e.g., end engaged to the mouthpiece 230) towards a second end (e.g., end engaged to the mixing unit 270). The collection chamber 218, the plunger 216 and the mixing unit 270 may be provided as a single unit or separate units.

In some embodiments, the disclosure relates to a method for measuring the in situ detection of a disease marker in a subject in need thereof, comprising, (a) activating the article described above by disengaging the first separator 108 to allow mixing between the vehicle 104 and the probe 110; (b) contacting a sample comprising the subject's EBC with the equipped article of (a) to facilitate an interaction between the probe 110 and the marker; and (c) detecting a signal generated from the interaction between the probe 110 and the marker. Under this embodiment, the signal may be a chemiluminescent or fluorescent signal. The method may include detection of a plurality of markers comprising a first marker which is hydrogen peroxide or a derivative thereof and optionally a second marker selected from hydrogen ions ($H^+$), pH, malondialdehyde, 8-isoprostanes, thiobarbituric acid reactive substances (TBARS), acetone, nitrosothiols, and nitric oxide-derived products.

In some embodiments, the disclosure relates to a method of diagnosing a pulmonary disease in a subject in need thereof, comprising activating the article by mixing the vehicle 104 with the probe 110; contacting the subject's exhaled breath condensate (EBC) sample with the activated article for a period sufficient to permit interaction between the probe 110 and a pulmonary disease marker present in the EBC; and detecting a signal generated from the interaction between the probe 110 and the marker. Under this embodiment, the pulmonary disease may be asthma, chronic obstructive pulmonary disease (COPD), idiopathic pulmonary disease (IPF), acute respiratory distress syndrome (ARDS) and the marker may comprise hydrogen peroxide or a derivative thereof. The method may include optionally detecting a second marker selected from hydrogen ions ($H^+$), malondialdehyde, 8-isoprostanes, thiobarbituric acid reactive substances (TBARS), acetone, nitrosothiols, and nitric oxide-derived products.

In some embodiments, the disclosure relates to the combined diagnosis and treatment of a pulmonary disease in a subject, comprising, first detecting the marker in a sample obtained from a subject and determining the subject to be suffering from the pulmonary disease by comparing to a control (e.g., a predetermined value or marker levels in a healthy subject); determine that the subject is suffering from the pulmonary disease if the marker levels or activity is higher in the subject's sample compared to the control; and administering a therapeutic composition to subjects who are determined to suffer from the pulmonary disease. Under one embodiment, the pulmonary disease may be asthma, COPD or IPF, wherein the marker is hydrogen peroxide or a derivative thereof selected from peroxide anion ($O_2^{-2}$), or a peroxide radical ($^{\cdot}OH$); and the subject is determined to suffer from the pulmonary disease if the level of hydrogen peroxide or a derivative thereof is elevated in the subject's sample compared to the level of hydrogen peroxide or a derivative thereof in the control sample; and a therapeutic composition for the treatment of the pulmonary disease is administered to the subjects who have been determined to suffer from the pulmonary disease.

In some embodiments, the disclosure relates to a method for measuring the in situ detection of a disease marker in a subject in need thereof, comprising, employing a system described above, e.g., a system comprising (A) a collection unit comprising a collection chamber 218 which is engaged with a plunger 216 at a first end and a mixing unit 270 at a second end; (B) a mouthpiece 230 which is engaged with the collection chamber via an inlet 241 and an outlet 242, each of which optionally comprises valves 239 and 240; and (C) a cooling device 237 which is engaged with an outer surface of the collection chamber, wherein the cooling device covers a substantial portion of the collective chamber, and wherein, the mixing unit 270 comprises (a) a vehicle chamber 202 containing a vehicle 204 for a probe 210 for the detection of the marker; (b) an auxiliary chamber that is physically separated from the vehicle chamber 202 via a first separator 208, wherein the auxiliary chamber contains the probe 210 that is specific to the marker; and (c) a reaction chamber 220 that is physically separated from the vehicle chamber 202 or the auxiliary chamber 206 or both the reaction chamber 220 and the auxiliary chamber 206 via a second separator 222, wherein the reaction chamber 220 contains a surface 224 for detection of the interaction between the probe 210 and the marker, and wherein the system optionally comprises (D) a receptacle 280 comprising a well, which is capable of engaging with the mixing unit 270 and which comprises a reader 234 and a vortex mixer 235. The detection method may be carried out by (a) activating the article described above by disengaging the first separator 208 to allow mixing between the vehicle 204 and the probe 210; (b) contacting a sample comprising the subject's EBC with the equipped article of (a) to facilitate an interaction between the probe 210 and the marker; and (c) detecting a signal generated from the interaction between the probe 210 and the marker. Under this embodiment, the signal may be a chemiluminescent or fluorescent signal. The method may include detection of a plurality of markers comprising a first marker which is hydrogen peroxide or a derivative thereof and optionally a second marker selected from hydrogen ions ($H^+$), pH, malondialdehyde, 8-isoprostanes, thiobarbituric acid reactive substances (TBARS), acetone, nitrosothiols, and nitric oxide-derived products.

To understand the present disclosure, it will now be described by way of example, with reference to the accompanying drawings in which implementations of the disclosures are illustrated and, together with the descriptions below, serve to explain the principles of the disclosure.

BRIEF DESCRIPTION OF THE DRAWINGS

The details of one or more embodiments of the disclosure are set forth in the accompanying drawings/tables and the description below. Other features, objects, and advantages of the disclosure will be apparent from the drawings/tables and detailed description, and from the claims.

FIG. 2A-2I show schematic diagrams of the systems of the disclosure and/or the various components contained therein. FIG. 2A shows a schematic diagram of a manifold containing the article of FIG. 1 and a collection unit 200 according to exemplary embodiments of the present disclosure. FIG. 2B shows a schematic diagram of cross-sectional view of the collection unit 260, the mixing unit 270 and the receptacle 280 and details the manner in which the various components are engaged in an exemplary device of the disclosure. FIG. 2C shows a schematic diagram of an outside view of the collection unit 260, the mixing unit 270 and the receptacle 280. FIG. 2D shows a schematic diagram of an outer view of the collection unit 260, the mixing unit 270 and part of the receptacle 280 that is engaged with the mixing unit, showing how various components of the mixing unit 270 align inside a well of the receptacle. FIGS. 2E-1 and 2E-2 show schematic diagrams of outer views of the collection unit 218 and the mouthpiece 230. Including various components thereof. FIG. 2E-1 shows the collection unit 218 and the mouthpiece 230 in assembled form; FIG. 2E-2 shows the collection unit 218 and the mouthpiece 230 in disengaged form. FIGS. 2F-1, 2F-2 and 2F-3 show schematic diagrams of cross-sectional views of the cooling unit 237. FIG. 2F-1 shows a dual-cylinder cooling unit 237 connected to a power source via an inlet 248. FIG. 2F-2 shows a blow-up view of the cooling unit showing the various components contained in a typical cooling unit. FIG. 2F-3 shows an assembled view of the cooling unit showing the various components contained therein. FIGS. 2G-1 and 2G-2 show assembly of the collection unit 218 and the cooling unit 237, wherein FIG. 2G-1 shows the individual units in disassembled form and FIG. 2G-2 shows the individual units in assembled form. FIG. 2H shows a schematic diagram of various components of a mixing unit 270. FIG. 2I shows a schematic diagram of a cross-sectional view of the collection unit 218, the mouthpiece 230, and the cooling device 237.

FIG. 3A shows a receptacle system whose lid is closed and FIG. 3B shows a receptacle system whose lid is open.

FIGS. 4A-4E show diagrams of manifolds comprising the article of FIG. 1 and FIG. 2H fitted with a collection unit 400 comprising a mouthpiece 430 according to exemplary embodiments of the present disclosure. FIG. 4A shows the manner in which the collection unit 400 is engaged with the receptacle. FIG. 4B shows a representative twisting mechanism that may be used to lock the collection unit 400 in the well of the receptacle and/or activate the detection system. FIG. 4C and FIG. 4D are identical to FIG. 4A and FIG. 4B, except they highlight slightly varied receptacles containing a frontal screen/LED display system. FIG. 4E shows the manner in which the mixing chamber 470 is engaged with the well 402 in the receptacle.

DETAILED DESCRIPTION

Various aspects now will be described more fully hereinafter. Such aspects may, however, be embodied in many different forms and should not be construed as limited to the embodiments set forth herein; rather, these embodiments are provided so that this disclosure will be thorough and complete.

Where a range of values is provided in this disclosure, it is intended that each intervening value between the upper and lower limit of that range and any other stated or intervening value in that stated range is encompassed within the disclosure. For example, if a range of 1 μM-8 μM is stated, it is intended that 2 μM, 3 μM, 4 μM, 5 μM, 6 μM, and 7 μM are also disclosed.

The singular forms "a," "an," and "the" include plural referents unless the context clearly dictates otherwise. Thus, for example, reference to a "vehicle" includes a single vehicle 104 as well as two or more of the same or different vehicles, and the like.

The word "about" means a range of plus or minus 10% of that value, e.g., "about 50" means 45 to 55. Furthermore, the phrases "less than about" a value or "greater than about" a value should be understood in view of the definition of the term "about" provided herein.

As used herein, the phrase "at least one of" preceding a series of items, with the terms "and" or "or" to separate any of the items, modifies the list as a whole, rather than each article of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Figure 1:
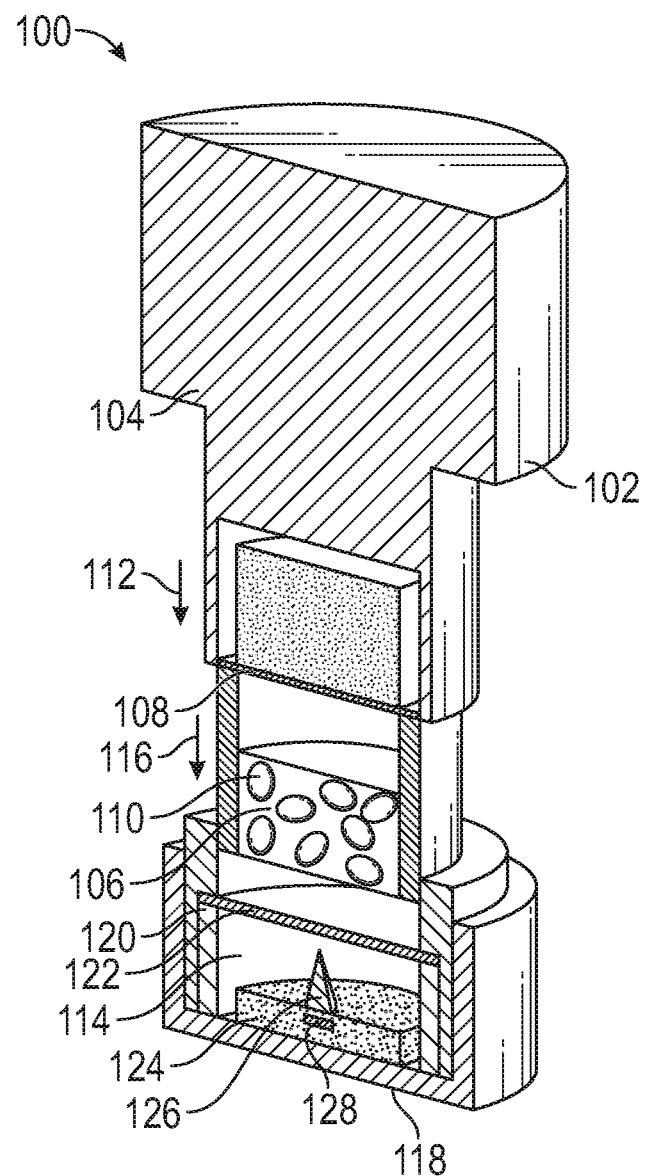
FIG. 1 shows a cross-sectional view of the article according to exemplary embodiments of the present disclosure.

In one embodiment, the disclosure relates to an article for measuring a disease marker in EBC. An exemplary article is shown in FIG. 1 and FIG. 2. The article may be formed from any suitable material, including, but not limited to, plastic, vinyl, polyethylene, rubber, platinum-cured silicon, fluorine-containing polymer (e.g., TEFLON®), metal, or a combination of materials. See, U.S. Pat. No. 7,828,741. In some embodiments, the material is chemically-resistant, e.g., Ethylene chloro-trifluoro ethylene (ECTFE; HALAR®), synthetic mica-filled polytetrafluoroethylene (PTFE) (FLUOROSINT®), high-density polyethylene (HDPE), nylon, polypropylene, polyphenylene sulfide (PPS), PTFE, low-density polyethylene (LDPE), polymethylpentene (PMP), fluorinated ethylene propylene (FEP), tetrafluoroethylene (TFE), polyfluoroalkoxy (PFA), ethylene-tetrafluoroethylene (ETFE). For example, the housing may be comprised of a strong plastic, such as high density polyethyelene or the like.

In one embodiment, the article 100 is a multi-chambered article comprising three chambers—a vehicle chamber 102, an auxiliary chamber 106, and a reaction chamber 120. The chambers may be provided in an integrated form. For example, the auxiliary chamber 106 may be connected to the vehicle chamber 102 but physically separated therefrom via a first separator 108 at a first end and also connected to the reaction chamber 120, but physically separated therefrom via a second separator 122, at a second end. Alternately, the chambers may be provided separately, in which case, the chambers are assembled as described above to generate the article prior to use. An exemplary article showing the interconnection between the chambers is shown in FIG. 1. The article 100, in its fully assembled state, comprises the vehicle chamber 102 separated from the auxiliary chamber 106 via a first separator 108 and a reaction chamber 120 separated from the auxiliary chamber 106 via a second separator 122.

In some embodiments, the vehicle chamber 102 contains a vehicle 104 for a probe 110 that is specific for the marker. Suitable vehicles 104 include any organic solvent, including, e.g., acyclic or cyclic ethers, such as ethylene glycol ethers, diethyl ether, diamyl ether, diphenyl ether, anisole, tetrahydrofuran, and dioxane, esters such as ethyl acetate, acetone, acetonitrile, propyl formate, amyl acetate, dialkyl esters of phthalic acid (e.g., dimethyl phthalate, diethyl phthalate, dibutyl phthalate, dioctyl phthalate), methyl formate, triacetin, diethyl oxalate, dioctyl terephthalate, dicyclohexyl phthalate, citric acid esters, methyl benzoate, ethyl benzoate, and butyl benzoate, aromatic hydrocarbons, such as benzene, ethyl benzene, butyl benzene, toluene, and xylene, chlorinated hydrocarbons, such as chlorobenzene, o-dichlorobenzene, m-dichlorobenzene, chloroform, carbon tetrachloride, hexachloroethylene, tetrachloro-tetrafluoropropane, and the like. The primary criterion for selecting the vehicle 104 is a substance suitable for maintaining the probe 110 in a stable, homogeneous liquid state. Additionally, vehicles may include ionic liquids. See, U.S. Pat. No. 7,060,169. The primary vehicle 104 is ethyl acetate (EtOAc), acetone, or acetonitrile ($CH_3CN$), or a mixture thereof, e.g., a mixture of ethyl acetate and acetone or a mixture of ethyl acetate and acetonitrile, e.g., in a ratio of between 19:1 and 1:1, particularly in a ratio between 9:1 to 4:1.

Since the vehicle 104 is preferably an organic solvent, it is desirable to employ materials that are resistant to the vehicle 104, e.g., polytetrafluoroethylene (PTFE), ultra-high-molecular-weight polyethylene (UHMW), high-density polyethylene (HDPE), polyphenylene sulfide (PPS), or NYLON66 (e.g., polymer of hexamethylenediamine and adipic acid), all of which show excellent resistance to organic solvents such as carbon tetrachloride, dibutylphthalate ether, diethyl ethyl acetate, ethylene glycol, etc. See, U.S. Pat. No. 9,636,044.

The article further comprises an auxiliary chamber 106 made from any material, e.g., glass, plastic, rubber, metal, natural or synthetic polymers, etc., although synthetic polymers are preferred. The auxiliary chamber 106 may be made from a material that is identical to or different from the material that is used to make the other chamber. Preferably, the auxiliary chamber 106 is made up of a material that is thermally stable and/or chemically inert. For this purpose, materials such as thermoplastics, e.g., polyvinylidene difluoride (PVDF), polyether ether ketone (PEEK), polyvinyl chloride, including halogenated variants thereof, e.g., chlorinated polyvinyl chloride (CPVC), glass, ceramic, or a combination thereof may be employed. See, U.S. Pat. No.

5,465,728, which discloses article constructed from components such as glass, stainless steel, and plastics, which do not out-gas volatile organic compounds in the condensate.

The auxiliary chamber 106 is physically separated from the vehicle chamber 102 by a first separator 108. The separator separates or compartmentalizes the vehicle 104 from the probes 110, which are contained in the auxiliary chamber 106. The reasons for this are two-fold—first, the physical separation allows a user to activate the probes only when needed, for example, when a test is initiated; second, the retention of probes in crystalline or solid state reduces (and even eliminates) loss due to heat, temperature, moisture, decomposition, self-activation, etc., which normally plague solution- or sol-based systems.

The separator 108, 122 may be made from a thin barrier material (e.g., a laminated foil with a thermoplastic layer). The separator can be attached to the chamber via an appropriate method, such as ultrasonic welding or heat-sealing. As necessary, more extensive barrier materials can be affixed after the vehicle chamber 102 is filled with the vehicle 104. Optionally, depending on the material requirements of the vehicle 104, barrier materials can be attached directly to the chamber through pressure sensitive adhesives, thermally set adhesives, or other methods (note that the chamber does not need to be constructed of thermoplastic materials). A variation on this design uses a thick-walled plastic cylinder as the body of the ampoule (housing the individual chambers) and is sealed on both ends with penetrable barrier materials. Preferably, the separator comprises a thin plastic or a metal foil, e.g., tin or aluminum foil.

In an alternate embodiment, the separator 108 may be gated, e.g., via valves that regulate flow rate. Representative examples of such valves used in ampoules include gate valves, diaphragm valves and the like. See, U.S. Pat. No. 9,357,946, which discloses breath condensate sub-systems containing valves. Another representative type is described in Konstantinidi et al., *Scientific World Journal*, 2015: 435160, 2015. In such embodiments, the valves may be automatically or manually opened and closed. For example, in certain embodiments, a user may open the first valve allowing the vehicle 104 and the probe 110 to mix to yield the activated probe 110; obtain a subject's EBC in the article; and then open a second valve allowing the EBC and the activated probe 110 to interact. In other embodiments, the valve timing is automated, either set by the clinician, or based on automatic determinations of when enough sample has been collected for a particular measurement. Valves may be placed anywhere appropriate.

The separator 108 may be provided separately from the individual components or together with the components. For instance, the first separator 108 may be provided separately, as a part of the vehicle chamber 102 or as a component of the auxiliary chamber 106 or as part of both the vehicle and the auxiliary chambers 102 and 106.

The auxiliary chamber 106 contains one or more probes 110. The probe 110 compound can be any compound or blend (e.g., mixture) of compounds in solid or liquid form which, when reacted with hydrogen peroxide, emit light. In one embodiment, the probe 110 includes a peroxide-reacting chemical (C) and a dye (D). Typically, probes will produce light having an emission spectrum between 330-1200 nm when reacted with hydrogen peroxide. Preferably, the emission spectrum is between 400-700 nm. Representative examples of probes are known in the art and are described in "Fluorescence and Phosphorescence," by D. Rendell, John Wiley & Sons Inc., New York, N.Y., 1987. Additional light-emitting compounds are disclosed in U.S. Pat. Nos. 3,749,679 and 6,126,871 incorporated herein by reference. Commercially available compounds such as luminol (5-amino-2,3-dihydrophthalazine-1,4-dione or 3-aminophthalhydrazide) and CYALUME® (containing diphenylethandioate, a dye, and other components) will react with hydrogen peroxide to produce light in the visible spectrum. Other examples of peroxide-reactive materials include: 2,4, 5-triphenylimidazole (lophine), 10,10'-dialkyl-9,9'-biacridinium salts (lucigenin), and 9-chlorocarbonyl-10-methyl-acridinium chloride (rosigenin).

In general, the peroxide reactive chemicals (C) are described in U.S. Pat. No. 8,647,579. In one embodiment, the peroxide reactive compound is an oxalate. Oxalates suitable for use in the current disclosure include, but are not limited to, bis(2-nitrophenyl) oxalate, bis(2,4-dinitrophenyl) oxalate, bis(2,6-dichloro-4-nitrophenyl) oxalate, bis(2,4,6-trichlorophenyl) oxalate, bis(3-trifluoromethyl-4-nitrophenyl) oxalate, bis(2-methyl 4,6-dinitrophenyl) oxalate, bis(1,2-dimethyl-4,6-dinitrophenyl) oxalate, bis(2,4-dichlorophenyl) oxalate, bis(2,5-dinitrophenyl) oxalate, bis(2-formyl-4-nitrophenyl) oxalate, bis(pentachlorophenyl) oxalate, bis(pentafluorophenyl) oxalate, bis(1,2-dihydro-2-oxo-1-pyridyl) glyoxal, bis-N-phthalmidyl oxalate, bis(2,4,5 trichloro-6-carbopentoxyphenyl) oxalate, bis(2,4,5-trichloro-6-carbobutoxyphenyl) oxalate, bis(2,4,6-trichlorophenyl) oxalate, and phthalimido 3,6,6-trisulfo-2-naphthyl oxalate. A preferred oxalate would be bis(2-carbopentyloxy-3,5,6-trichlorophenyl) oxalate. In another embodiment, the peroxide reactive compound is an oxamide. Oxamides suitable for use in the current disclosure are known in the art, e.g., N,N'-bis(2,4,5-trichlorophenyl)-N,N'-bis(trifluoromethylsulfonyl) oxamide. See, U.S. Pat. Nos. 4,226,738 and 4,407,743.

In particular, the preferred peroxide reactive chemical (C) is selected from the following non-limiting group of compounds: bis(2-carbopentyloxy-3,5,6-trichlorophenyl) oxalate, bis(2,4,5 trichloro-6-carbopentoxyphenyl) oxalate, bis(2,4,6-trichlorophenyl) oxalate, bis(pentafluorophenyl) oxalate, and bis(2,4-dinitrophenyl) oxalate. With the most preferred peroxide reactive compound being bis(2,4,5-trichloro-6-carbopentoxyphenyl) oxalate.

Suitable dyes (D) include anthracenes and derivatives thereof such as but not limited to benzanthracene, phenanthrene, naphthacene, pentacene, substituted derivatives thereof and the like. Examples of substituents include phenyl, lower alkyl, halide, cyano, alkoxy, and other substituents which do not interfere with the light-emitting reaction described herein. Specific examples of anthracene type compounds include anthracene, diphenylanthracene (DPA), or 9,10-bis(phenylethynyl) anthracene, bis(phenylethynyl)anthracene (BPEA), and rubrene. Conjugated fluorescing polymers such as but not limited to poly(phenyleneethynylene), poly(phenylene-vinylene), poly(p-phenylene), polythiophene, substituted derivatives thereof and the like also perform satisfactorily in the current disclosure. Further, anthracene derivatives covalently bonded to an iptycene, such as the compound provided below, are suitable for use as the dye component. The preferred dye is 9,10-bis(phenylethynyl)anthracene.

As noted above, the probes may comprise any luminescent material, including chemiluminescent dyes, oligomers, polymers, combinations thereof, etc. The probe 110 may be selected to exhibit certain properties, such as a particular emission wavelength, high quantum yield, and/or compatibility (e.g., solubility) with one or more components of the chemiluminescent material. For example, the probe 110 may be selected to be soluble with respect to a solvent or other vehicle 104 to form mixtures (e.g., solutions) having a relatively high concentration or saturation of the probe 110. In some embodiments, the probe 110 may be selected to exhibit a high quantum yield, for example, when present in a solution having a high concentration of probe 110. As used herein, the "quantum yield" of a material refers to the total emission produced by the material, i.e., the number of photons emitted per adsorbed photon. For example, the quantum yield of the probe 110 may refer to the amount of light emission produced (e.g., light output). In some cases, the probe 110 may have a quantum yield of at least 20%, at least 50%, at least 75%, at least 90%, at least 95%, or, in some cases, at least 99% or greater. Methods of determining quantum yields of dyes such as anthracene derivatives are outlined in Gray et al. (*J. Mater. Chem. C*, 3, 11111-11121, 2015).

The probe 110 may also include, for example, conjugated polymers (P) such as poly(arylene)s, poly(phenylene vinylene)s and poly(phenylene ethynylene)s. In some embodiments, the probe 110 is fine crystalline, which may improve various properties of the materials including solubility and/or emissive properties of the materials. As used herein, a "fine crystal" is a solid material whose constituents (such as molecules) are arranged in a highly ordered microscopic structure, forming a crystal lattice that extends in all directions. Crystalline forms of dyes comprising salts thereof in greater than 97% purity are preferred.

In certain embodiments, the probe 110 composition optionally includes a catalyst (K). A preferred catalyst is imidazole. The catalyst is selected for its ability to improve the reaction rate between the probe 110, particularly the peroxide reactive chemical (C), and $H_2O_2$. Other suitable catalysts include but are not limited to: tetrabutylammonium salicylate, potassium salicylate, lithium salicylate, tetrahexylammonium benzoate, benzyltrimethylammonium m-chlorobenzoate, tetraethyl ammonium stearate, calcium stearate, magnesium stearate, lithium stearate, triethylamine, pyridine, piperidine, sodium salicylate, potassium trichlorophenoxide.

If the optional catalyst is included for the detection of EBC hydrogen peroxide, it is preferably selected from the following non-limiting group of compounds: imidazole, sodium salicylate, lithium salicylate, and tetrabutylammonium salicylate, wherein sodium salicylate and imidazole are particularly preferred. Alternately, the catalyst may be omitted in favor of longer incubation times. Heating may also be employed to facilitate the reaction between $H_2O_2$ and the $H_2O_2$-reactive chemical.

Typically, the aforementioned components of the probe 110, e.g., dye (D), reactive chemical (C), catalyst (K), and/or polymer (P) are in solid phase, e.g., in crystalline or amorphous form. In some cases, the probe 110 may be coated onto a surface 124 so as to improve the surface area and to provide rapid dissolution in the vehicle 104. However, in some embodiments, the probe 110 comprises a liquid chemiluminescent material comprising an oxalate (e.g., bis(2-carbopentyloxy-3,5,6-trichlorophenyl)oxalate (CPPO), oxalic acid bis(2,4,6-trichlorophenyl oxalate (TCPO), a dye, i.e., the light-emitting component, (e.g., an anthracene dye comprising DPA or BPEA), and a solvent (e.g., a mixture of ethyl acetate and acetone and/or acetonitrile).

In one embodiment, the probes are activated in situ, e.g., via a reaction between the reactive chemical and the dye. As used herein, the term "in situ" refers to processes, events, objects, or components that are present or take place within the context of the system or device, including, the surrounding environment, for example, in the vehicle 104 with which the dyes and the reactive chemical comes into contact. As an example, an in situ reaction may refer to the reaction of the various components present in the device (e.g., dye, the reactive compound, the vehicle 104 and optionally the catalyst), including, with the components provided by the user (e.g., peroxide present in the EBC). The term is contrasted with ex situ, which refers to outside the environment.

In one embodiment, the probes are activated when dissolved in the vehicle 104. A variety of methods may be employed to bring the vehicle 104 in contact with probes 110. In one embodiment, a plunger system 112, 116 or 212, 216 is employed. Preferably, the article disclosed herein comprises a plunger assembly having a piston and a handle, wherein the piston is slidably disposed in the interior of the vehicle chamber 102 and wherein the handle extends from the first end of the central auxiliary chamber 106 so as to permit the piston to be moved within the central chamber, whereby the piston breaks one or more separators (or engages the elongated member 126 to pierce the separator). Once engaged, the plunger results in movement of the vehicle 104 into the auxiliary chamber 106, thereby, mixing with the probe 110 to generate an activated dye. A single plunger or a multi-stage plunger (e.g., a 2-stage plunger or a 3-stage plunger) may be used. In devices comprising the two stage plunger, a first plunger 112 is configured to remove the first separator 108 (as described above); while a second plunger 116 comprising a second piston and a handle is slidably disposed in the interior of the reaction chamber 120 and wherein the handle extends from the second end of the central auxiliary chamber 106 so as to permit the piston to be moved within the auxiliary chamber 106. Once engaged, the second plunger 116 results in movement of the activated probe 110 solution into the reaction chamber 120, wherein it can mix with the EBC sample 232 containing the marker to generate a signal. Exemplary devices with plungers are disclosed in, e.g., U.S. Pat. No. 7,828,741. Alternately, the movement of the liquid vehicle 104 (with or without the probe 110) may be facilitated via one or more of the following forces: gravity, electrokinetic, pneumatic pressure, fluid pressure, vacuum, thermal, osmotic, pumping, bimetallic disc membranes, etc.

The article further comprises a reaction chamber 120 that is physically separated from the vehicle chamber 102 or the auxiliary chamber 106 or both the reaction chamber 120 and the auxiliary chamber 106 via a second separator 122. The reaction chamber 120 may be made of any material, e.g., glass, plastic, rubber, metal, natural or synthetic polymers, etc. Preferably, the reaction chamber 120 is made from an optically transparent or translucent material, e.g., glass or plastic. U.S. Pat. No. 9,103,766 discloses some materials for optical monitoring, wherein the viewing portion is made from a transparent material such as glass.

In one embodiment, the article comprises a second separator 122, which, like the first separator 108, may be provided separately from the reaction and/or auxiliary chambers 106 and 120, or as a part of the reaction chamber 120, or as a part of the auxiliary chamber 106 or as part of both the reaction chamber 120 and the auxiliary chamber 106. Preferably, the second separator 122 is a part of the reaction chamber 120. The second separator 122 may be made from a material that is similar to the material used in making the first separator 108, e.g., thin plastic material or a metal foil, such as, tin foil or aluminum foil. Alternately, the second separator 122 may be gated, e.g., mechanically or electrically, as described previously.

The contents of the auxiliary chamber 106 may be moved into the reaction chamber 120 by utilizing a variety of methods. In one embodiment, the previously-described two-stage plunger system 112, 116 or 212, 216 is employed. Herein, the article is first charged by initiating the first plunger 112 or 212 to disengage the first separator 108 and dissolve the probe 110 in the vehicle 104. Briefly thereafter (e.g., less than 5 minutes, but preferably less than 2 minutes, and particularly less than 1 minute after initiation), an EBC sample 232 is collected via the mouthpiece 230. The second plunger 116 is initiated immediately after or contemporaneously with EBC sample 232 collection. The second plunger 116 disengages the second separator 122, resulting in the movement of the activated probe 110 into the reaction chamber 120.

Wherein the individual chambers are separated by membrane or film separators, the auxiliary chamber 106 or the reaction chamber 120 or both chambers may comprise one or more elongated members 126 (e.g., a needle, pin, nail, rod, and the like), which is used to dispense the contents of one chamber, either partially or wholly, into the other. In various aspects of the disclosure, the elongated member 126 creates a hole in the separator, allowing the contents of one chamber (e.g., activated probe 110 solution in the auxiliary chamber 106) to flow into the other chamber (e.g., reaction chamber 120). The dispensing function also involves moderating the pressure in the space above the initial fluid level as the fluid moves out of the liquid container so that the fluid moves out of the liquid container and into the reaction chamber 120. This preferably is accomplished by piercing or otherwise creating an opening in the space above the liquid so that gas can enter the space to equalize the pressure, to avoid creating a negative pressure or vacuum in the space, and to thereby permit the liquid to flow or otherwise move out of the chamber.

In particular embodiments or applications, it is desirable that the vehicle chamber 102, or at least the hole or holes in it through which the vehicle 104 containing the probe 110 is dispensed, be in close proximity to, and more preferably immediately adjacent to, the auxiliary chamber 106 and/or the reaction chamber 120. In such embodiments and applications, it is preferred, that a medium be provided at the exit hole or holes in liquid container to facilitate movement or flow of the liquid out of and away from the liquid container and toward the reaction zone, through wicking or capillary action. Accordingly, the vehicle chamber 102 may be separated from the reaction chamber 120 only by a narrow auxiliary chamber 106. It is also preferred that there are no air gaps or other spacing between those two chambers, except for the auxiliary chamber 106. To achieve this feature, the auxiliary chamber 106 may comprise a thin polyethylene disk, which is contiguous with the first separator 108 (e.g., foil) at the bottom of the vehicle chamber and which disk is contiguous with and open to a reaction surface 124 contained in the reaction chamber 120.

The reaction chamber 120 further contains a surface 124, which facilitates interaction between the activated probe 110 solution and the marker. The surface 124 may comprise the entire inner wall of the reaction chamber 120 or a portion thereof. For example, the surface 124 may be placed on an end that is connected to the collection unit (i.e., distal to the end connected to the auxiliary chamber 106). This placement may advantageously facilitate interaction between the EBC sample 232 and the activated probe 110. The surface 124 may be made from a solid, semi-solid or liquid material. The surface 124 may comprise a chemisorptive or a physisorptive material. Examples of solid or semi-solid surface materials include glass, silica, polymers, copolymers, gels, adsorbent materials such as charcoal, sponge, KIM WIPE®, filters, activated carbon, cellulose, lignin, polycaprolactone (PCL) or a combination thereof. In some embodiments, the surface 124 material may comprise finely divided powder, particles, or molded into shapes such as pads, beads, films, spheres, tubes, strips, tapes, layers, and the like (for example, by casting, molding, extruding, etc.). Preferably, the surfaces 124 are also pervious to the vehicle 104, e.g., an organic solvent. Preferably, the surface 124 is comprised of sponge, wool, glass filter paper, filter paper, nylon filters, and the like. Alternately, the surface 124 is made from a polymer selected from, e.g., polyethylene, polypropylene, poly(vinyl chloride), poly(methyl methacrylate), poly(vinyl benzoate), poly(vinyl acetate), cellulose, corn starch, poly (vinyl pyrrolidinone), polyacrylamide, epoxys, silicones, poly(vinyl butyral), polyurethane, nylons, polacetal, polycarbonate, polyesters and polyethers, crosslinked polymers such as polystyrene-poly(divinyl benzene), polyacrylamide-poly(methylenebisacrylamide), polybutadiene copolymers, or a combination thereof. In a particular embodiment, the polymer is charcoal, sponge or a synthetic sponge comprising cellulose or a derivative of cellulose.

In some embodiments, the surfaces 124 may be attached to a fluid conduit, thus allowing the vapor to condense and then flow into a fluid channel. The fluid channel could be part of a microfluidic system, where the fluid is processed and analyzed. Examples of carbon nanotube (CNT) detector systems for nitric oxide, carbon dioxide and other breath constituents are described in, e.g., U.S. Pat. Nos. 7,547,931; 8,366,630 and 6,010,459.

In some embodiments, the surface 124 may comprise a microfluidic device. Purely as an exemplary embodiment, a sketching of the microfluidic device (not to scale) is shown as structure 128 (FIG. 1) and structure 228 (FIG. 2). The microfluidic device can be a device through which materials, particularly fluid-borne materials, such as liquids, can be transported. In some embodiments, the materials are transported on a micro-scale (e.g., μL amount), and in some embodiments on a nanoscale (e.g., in nL amounts). An exemplary microfluidic device typically comprises dimensional features dimensioned on the order of a millimeter (mm) scale or less, which are capable of manipulating a fluid at a flow rate on the order of about 1 μL/min or less. Typically, such features include, but are not limited to channels, fluid reservoirs, reaction region, mixing region, and separation regions. In some examples, the channels include at least one cross-sectional dimension that is in a range of from about 0.1 μm to about 500 μm. The use of dimensions on this order allows the incorporation of a greater number of channels in a smaller area, and utilizes smaller volumes of fluids.

Figure 6:
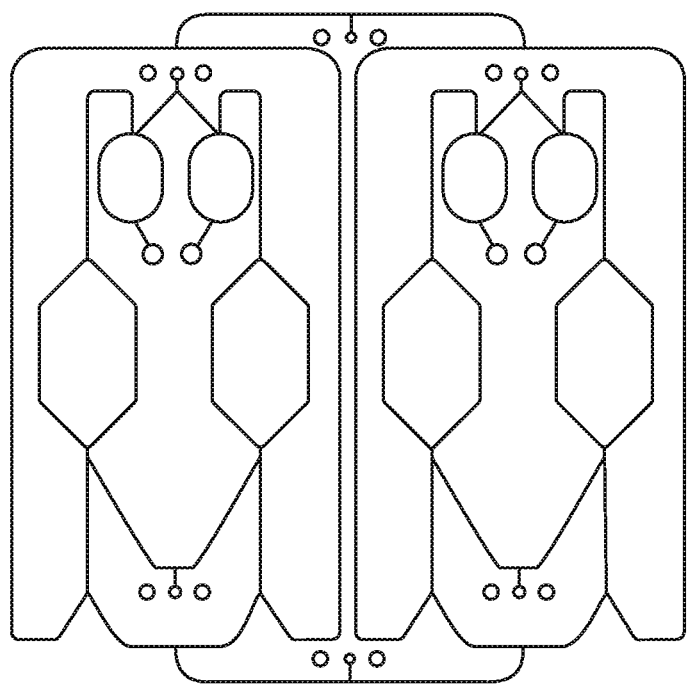
FIG. 6 shows the schematic architecture of a microfluidic chip that may be used in the detection chamber of the articles (optional). The microfluidic chip uses a plurality of gates and valves to control flow rates of reagents, mix and reconstitute reagents, and dispense the sample for testing. A set of syringe modules are fitted to the chip using Leur fittings and used to store reagents prior to testing as well as dispense the reagents, solvents, and buffers. The modules can be activated manually by the user, but preferably automatically by an actuating mechanism on the testing device. The modules are activated in a series of stages to first reconstitute the reagent solutions, and then to transfer to the final reaction chamber where the sample is mixed in at the time of testing. Alternatively, blister packs may be used in place of the syringe modules to store the reagents, and are punctured at the time of testing to activate. In this embodiment, a syringe module is still used to meter and dispense the sample. The microfluidic paths and chambers may be manufactured through injection molding or by being etched onto the chip. The microfluidic chip may be placed anywhere that permits contact with the EBC, such as, for example, on the surface of the reaction chamber.

An exemplary microfluidic device, e.g., X4 chip, is shown in FIG. 6. A plurality of microfluidic devices may also be employed. For example, microfluidic pumps for introducing fluids, such as, e.g., samples, reagents, buffers and the like, into the system and/or through the system may be used together with microfluidic control systems for controlling fluid transport and/or direction within the device; and other microfluidic components for monitoring and controlling environmental conditions, e.g., temperature, current, etc. A microfluidic device of the present disclosure may comprise one or more "channels," which comprise recesses or cavities formed in a material by imparting a pattern from a patterned substrate into a material or by any suitable material removing technique. In some embodiments, the cavities comprise any suitable fluid-conducting structure mounted in the recess or cavity, such as a tube, capillary, or the like.

The microfluidic devices may further comprise a "chip" to facilitate performance of the methods, assays, and diagnostic techniques of the present disclosure. In certain embodiments, a "chip" may refer to a solid substrate with a plurality of one-, two- or three-dimensional micro structures or micro-scale structures on which certain processes, such as physical, chemical, biological, biophysical or biochemical processes, etc., can be carried out. The micro structures or micro-scale structures such as, channels and wells, electrode elements, electromagnetic elements, are incorporated into, fabricated on or otherwise attached to the substrate for facilitating physical, biophysical, biological, biochemical, chemical reactions or processes on the chip. The chip may be thin in one dimension and may have various shapes in other dimensions, for example, a rectangle, a circle, an ellipse, or other irregular shapes. The size of the major surface of chips of the present disclosure can vary considerably, e.g., from about 40 $cm^2$ to about 500 $cm^2$ or from about 80 $cm^2$ to about 240 $cm^2$ and especially from about 100 $cm^2$ to about 200 $cm^2$. The dimension of the chip may also vary, e.g., from about 2 cm to about 50 cm, preferably from about 4 cm to about 20 cm and especially from about 8 cm to about 14 cm. The chips may of different shapes, e.g., rectangular, square, or the like. The chip surfaces may be flat, or not flat. The chips with non-flat surfaces may include channels or wells fabricated on the surfaces. The microfluidic chip can be made from any suitable material, e.g., polydimethylsiloxane (PDMS), glass, polymethylmethacrylate (PMMA), polyethylene terephthalate (PET), polycarbonate (PC), etc. An exemplary chip is shown in FIG. 6.

A microfluidic device of the present disclosure can include instrumentation such as one or more pumps, valves, fluid reservoirs, channels, sample ports, and/or reagent storage cells. Upstream or downstream pumps may be used to move the samples or reagents in the microfluidic device. The pump can drive each fluid sample or reagent to (and past) a specialized compartment within the microfluidic device. Alternatively, samples or reagents may be driven through the fluid by gravity or capillary action. The disclosure in the following documents provide information on the tools that can be used with the assay systems of the present disclosure, allowing for the precise manipulation of gases, liquids and solids to accomplish very complex analytical manipulations with relatively simple hardware: U.S. Pat. Nos. 9,110,029; 9,547,015; 6,877,892; 6,890,093; 6,916,113; 6,935,772; 7,223,371; 8,304,193; 8,329,407; 8,528,589; 8,592,221; 8,740,448; 8,772,046; 8,871,444; 9,068,699; 9,186,643; 9,328,344; 9,329,107; 9,410,151; 9,464,319; 9,498,759; and 9,562,837.

In one embodiment, the microfluidic chip of the disclosure defines a fluid mixer system having four commonly-fed but separate reaction systems arranged in parallel (representative illustration provided in FIG. 6). The reaction systems each employ a reaction chamber 120 wherein the chemiluminescent reactions to be measured occur. Each of four liquids are input into each reaction chamber 120 from supply reservoirs fluidly connected to corresponding input ports.

As outlined in FIG. 6, the microfluidic device of the disclosure comprises a plurality of ports, wherein first fluid (X1), comprising, e.g., a solution of anthracene dye, imidazole, and ethyl acetate and/or acetone solvent) is input to the chip at the upper, central port shown above from a first external reservoir. The input flow is divided into four flow channels. A second fluid (X2), comprising, e.g., solution of TCPO and ethyl acetate/acetone solvent) is similarly input to the chip at the lower, central port shown above from a second external reservoir. For each of the four reaction systems, a pre-mixture of first and second fluids is created by joining the fluid flows into a common pre-mixture channel. Each pre-mixture channel flows to an entry port of a reaction chamber 120. A third fluid (X3), comprising, e.g., buffer) is input to the chip from an external reservoir at two input ports (seen above at the lower left and right of the chip), with each flow then divided into two flow channels (four total). Each buffer fluid channel intersects a corresponding pre-mixture channel at the entry port to the reaction chamber 120. The buffer fluid acts primarily to "draw" the pre-mixture into the reaction chamber 120. Sample EBC is received from an external EBC reservoir through two EBC entry ports, with each flow then divided into two EBC channels (four total). Each EBC channel flows to an EBC entry port to a reaction chamber 120. Thus, each reaction chamber 120 receives a pre-mixture of anthracene dye, imidazole, TCPO, ethyl acetate/acetone, and buffer liquid through a primary entry port and EBC through a secondary, EBC entry port. Order of mixing of liquids is controlled through the content of the supply reservoirs, intersections of fluid channels, and entry into the reaction chamber 120.

The microfluidic device may be integrated or connected to the device (e.g., surface 124) via any means. In one embodiment, the material used in the surface forms a transparent upper layer of the microfluidic chip at least at the reaction chambers 120 such that reactive light is emitted through the transparent layer and to a photon or light detector or sensor. The entire microfluidic chip is likely to be encased or held by a larger "cassette" body/frame, creating an easily-handled chip unit for insertion and removal into the testing device. Each chip unit may be single-use or multi-use. Single-use chips are disposable, but multi-use chips may be recycled using routine methods for cleaning. The volumes and arrangement of various flow features (i.e., channels, chambers, etc.), are selected based on desired ratios of fluids for mixing and order of mixing.

FIG. 1 shows the cross-section of an exemplary article comprising the following components: (A) a vehicle chamber 102 containing a vehicle 104 that dissolves the probe 110; an auxiliary chamber 106 containing probes 110 for monitoring EBC markers, wherein the auxiliary chamber 106 is separated from the vehicle chamber 102 via a first separator 108; (C) a reaction chamber 120 containing a surface 124 (optionally containing a microfluidic chip) and an elongated member 126, wherein the reaction chamber 120 is separated from the auxiliary chamber 106 via a second separator 122. The article contains a plurality of plungers 112, 116, wherein the initiation of the first plunger 112 disengages the first separator 108 and initiation of the second plunger 116 disengages the second separator 122. The article may also include a protective cover surrounding the reaction chamber 120 that is made of thin transparent or translucent material 114 that is pervious to signal, e.g., fluorescent signal or chemiluminescent signal.

Figure 2A:
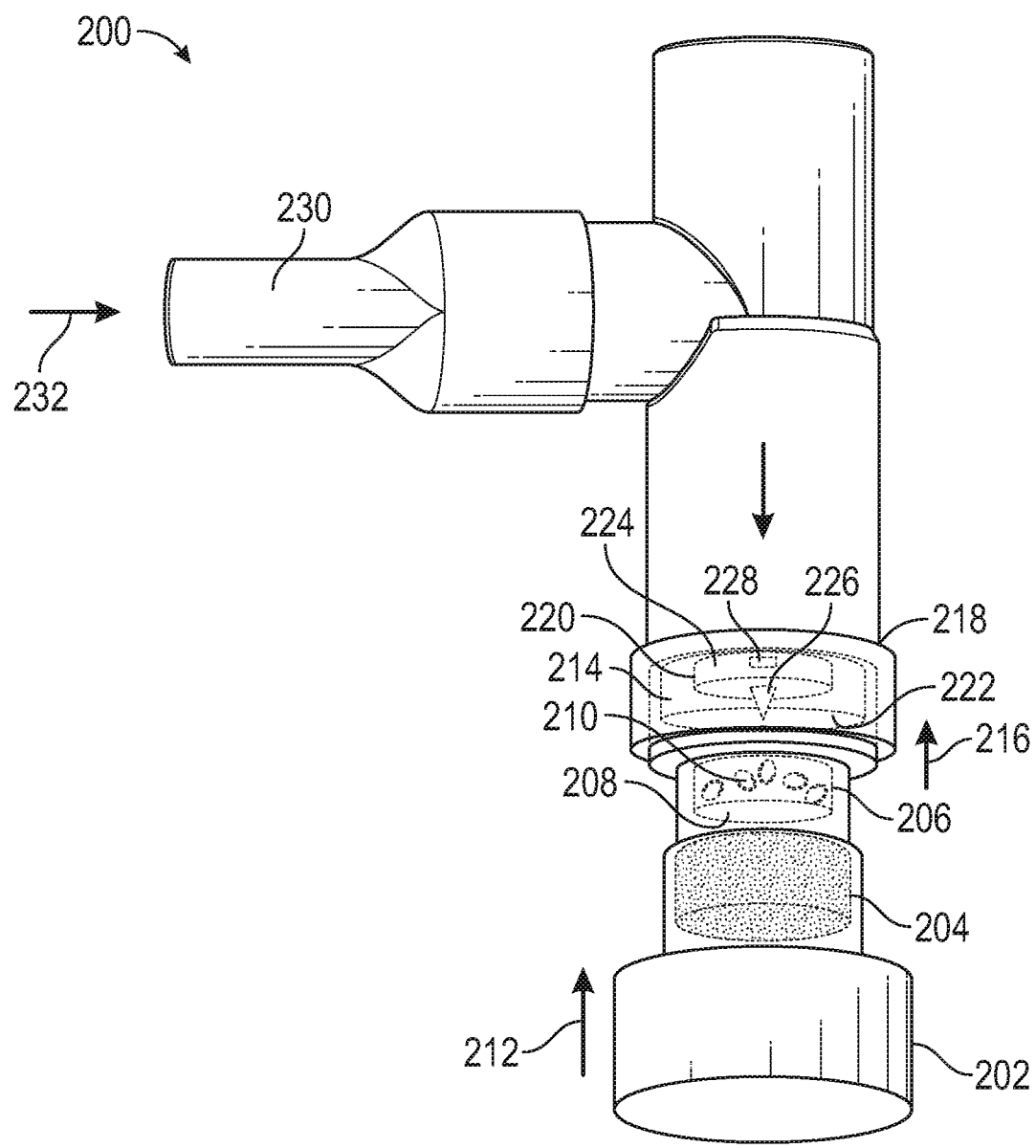

The analytical article described above may be coupled to one or more secondary articles. For instance, as shown in FIG. 2A, the article of the present disclosure may further include a collection unit comprising a mouthpiece 230 configured to receive breath 232 from a subject and a chamber for collecting the exhaled breath condensate 218. The mouthpiece and the collection chamber may form a single unit or may be provided separately. The collection unit may be T-shaped, L-shaped or S-shaped. A plurality of valves may be employed in the tube(s) connecting the mouthpiece 230 and the collection chamber 218. The collection unit may be made from any material. A conventional glass or plastic test tube, for example, is suitable as a disposable collection unit. The collection unit may also include removable insulation, electronic cooling, and/or chemical cooling systems.

An exemplary T-shaped collection unit is shown in FIG. 2A. The collection unit 200 has a mouthpiece 230 for collecting the EBC 232 from a user/subject and a distal end 218 that is affixed to the article of FIG. 1 (inverted in orientation in FIG. 2A compared to FIG. 1). The article is charged for use immediately prior to, contemporaneously with, or upon transmission of an EBC sample 232 into the collection unit 200. First, a first plunger 212 is initiated, thereby disengaging the first separator 208 and allowing the vehicle 204 in the vehicle chamber 202 to mix with the probe 210 in the auxiliary chamber 206. Second, the vaporous EBC is forced into the main reaction chamber 220 with a plunger and a second plunger 216 is initiated to force the probe solution into the reaction chamber 220. Upon reaction with the markers in the vaporous EBC, the analyte generates a signal which can be detected.

The mouthpiece 230 article preferably includes a mouthpiece 230, which may be formed so that a subject may comfortably exhale from the user's mouth and/or nose into the mouthpiece 230. The mouthpiece 230 preferably also includes a first one-way valve configured to permit air to be drawn into the mouthpiece 230 article by a subject, and a second one-way valve configured to permit air to pass from the mouthpiece 230 to a distal end of the mouthpiece 230. A particle or other type of filter may be positioned in the mouthpiece 230 between the mouthpiece 230 and the distal end of the mouthpiece 230. Preferably, the filter is pervious to air and/or vapor but impervious to liquid. This ensures that the chemical probes 110 and the vehicles thereof do not leak or overflow into the collection unit and/or the mouthpiece 230 during the collection and/or enrichment procedure. Representative types of mouthpieces and collection units are described in, e.g., U.S. Pat. Nos. 5,042,501; 5,787, 885; and 8,211,035.

In one embodiment, the collection unit comprises a commercially-available mouthpiece 230 e.g., a RESPIRGARD II nebulizer (Vitaly Medical, Inc., Salt Lake City, Utah; Item #124030). The mouthpiece 230 includes a mouthpiece 230, first and second one-way valves and a 0.3 μm particle filter and is optionally surrounded by a plastic tube (a XERI-TUBE 700™ from Rain-Bird, Inc. of Glendora, CA).

Alternatively or additionally, the collection units may contain a nosepiece. The nose is an anatomical, physiological dehumidifier and samples may be collected therefrom to prevent dehydration during normal respiration.

In one particular embodiment of the present disclosure, an EBC marker detection system is provided. The EBC marker detection system includes an article (FIG. 1 and FIG. 2A) comprising a vehicle chamber 102, 202 that contains a vehicle 104, 204; an auxiliary chamber 106, 206 connected to the vehicle chamber 102, 202 but separated therefrom via a first separator 108, 208, wherein the auxiliary chamber 106, 206 contains a probe 110, 210 that is specific for the marker; and a reaction chamber 120, 220 that is connected to a mouthpiece 230 (FIG. 2A) via a first end 118, 218 and the auxiliary chamber 106, 206 via a second end, wherein the reaction chamber 120, 220 is separated from the auxiliary chamber 106, 206 via a second separator 122, 222 located in the second end, wherein the reaction chamber 120, 220 provides a surface 124, 224 for the reaction between the EBC marker and the probe 110, 210 to generate a signal. In some embodiments, the signal may be processed and/or detected with a microfluidic chip, which may be placed anywhere in the reaction chamber, e.g., the surface 124, 224. The reaction chamber is optionally provided with a window 114, 214, which allows a user to monitor the reaction between the EBC marker and the activated probe 110, 220. In some implementations, the article contains one or more plungers 112, 116 and 212, 216. Herein, initiation of a first plunger 112, 212 disengages the first separator 108, 208, allowing the vehicle 104, 204 in the vehicle chamber 102, 202 to enter the auxiliary chamber 106, 206 and solubilize and activate the probe 110, 210 contained therein. Also, initiation of a second plunger 116, 210 disengages the second separator 112, 212, e.g., via penetration of the second separator 112, 212 by the elongated member 126, 226, allowing the activated probe solution in the auxiliary chamber 106, 206 to enter the reaction chamber 120, 220 and react with the EBC marker collected therein. The reaction between the EBC marker and the activated probe solution 110, 210 may take place on the surface 124, 224 which allows for in situ detection of the signal without the need for freezing, processing and/or transporting the EBC sample 232 (FIG. 2A).

Figure 2B:
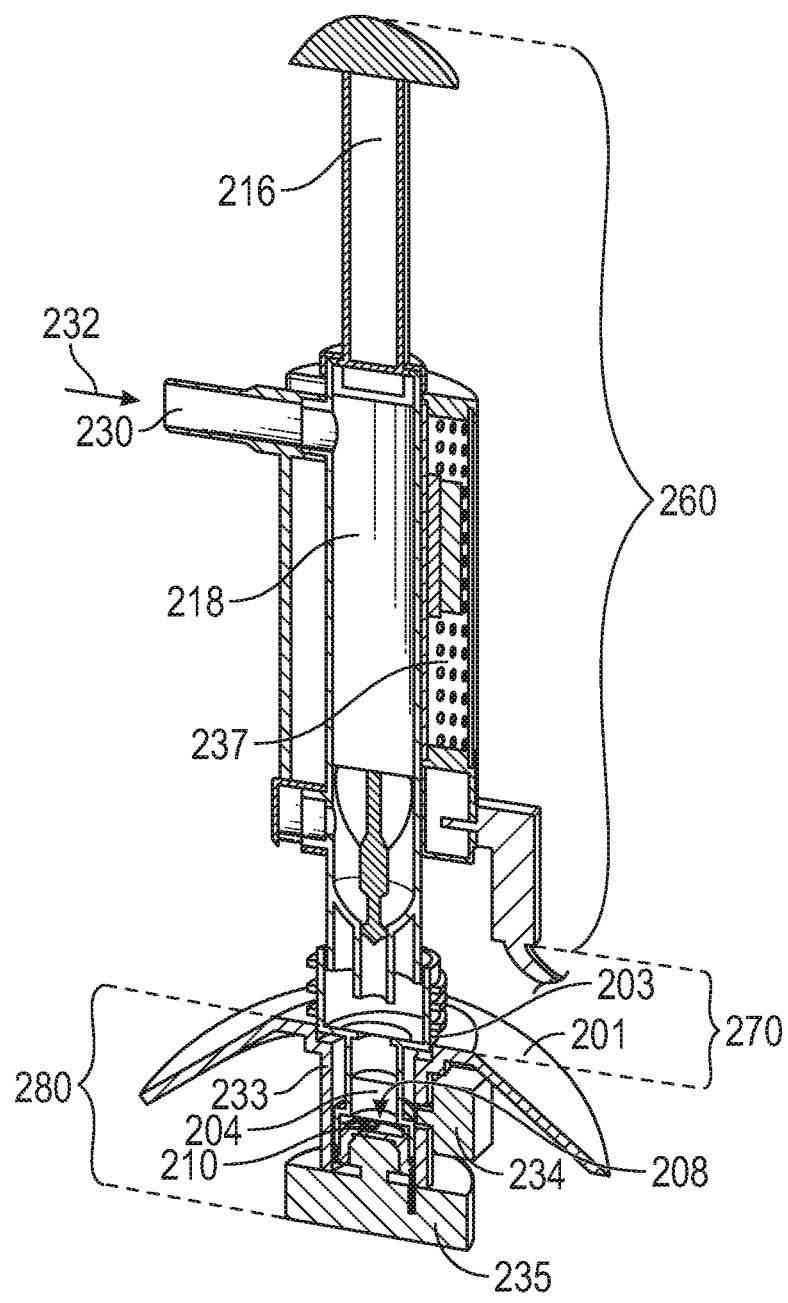

FIG. 2B shows a schematic diagram of cross-sectional view of the collection unit 260, the mixing unit 270 and the receptacle 280 and details the manner in which the various components are engaged in an exemplary device of the disclosure. For instance, collection unit 260 may contain a collection chamber 218 which is housed inside a cooling device 237 (either completely or substantially). A mouthpiece 230 may be appended onto the collection unit 218 via an inlet such that EBC 232 may be introduced into the collection unit 218. The collection unit may contain a plunger 216 on one end, which, when engaged, propels the EBC from the mouthpiece 230 area to towards the distal end of the collection unit 218, which is engaged with a mixing unit 270. Mixing unit 270 comprises a vehicle chamber that contains a vehicle 204; an auxiliary chamber connected to the vehicle chamber but separated therefrom via a first separator 208, wherein the auxiliary chamber contains a probe 210 that is specific for the marker; and a reaction chamber that is connected to the collection chamber and the auxiliary chamber, wherein the reaction chamber is separated from the auxiliary chamber via a second separator located in the second end, wherein the reaction chamber provides a surface for the reaction between EBC markers and the probe 210 to generate a signal. Mixing unit 270 can be slotted into a well of the receptacle 280, which contains a vortexer 235 (for mixing the reaction components, e.g., dye (D), reactive chemical (C), catalyst (K), and/or polymer (P) with the EBC marker (M). Receptacle 280 also contains a reader 234 for reading the signal (S) generated via a reaction between the reaction components.

Figure 2C:
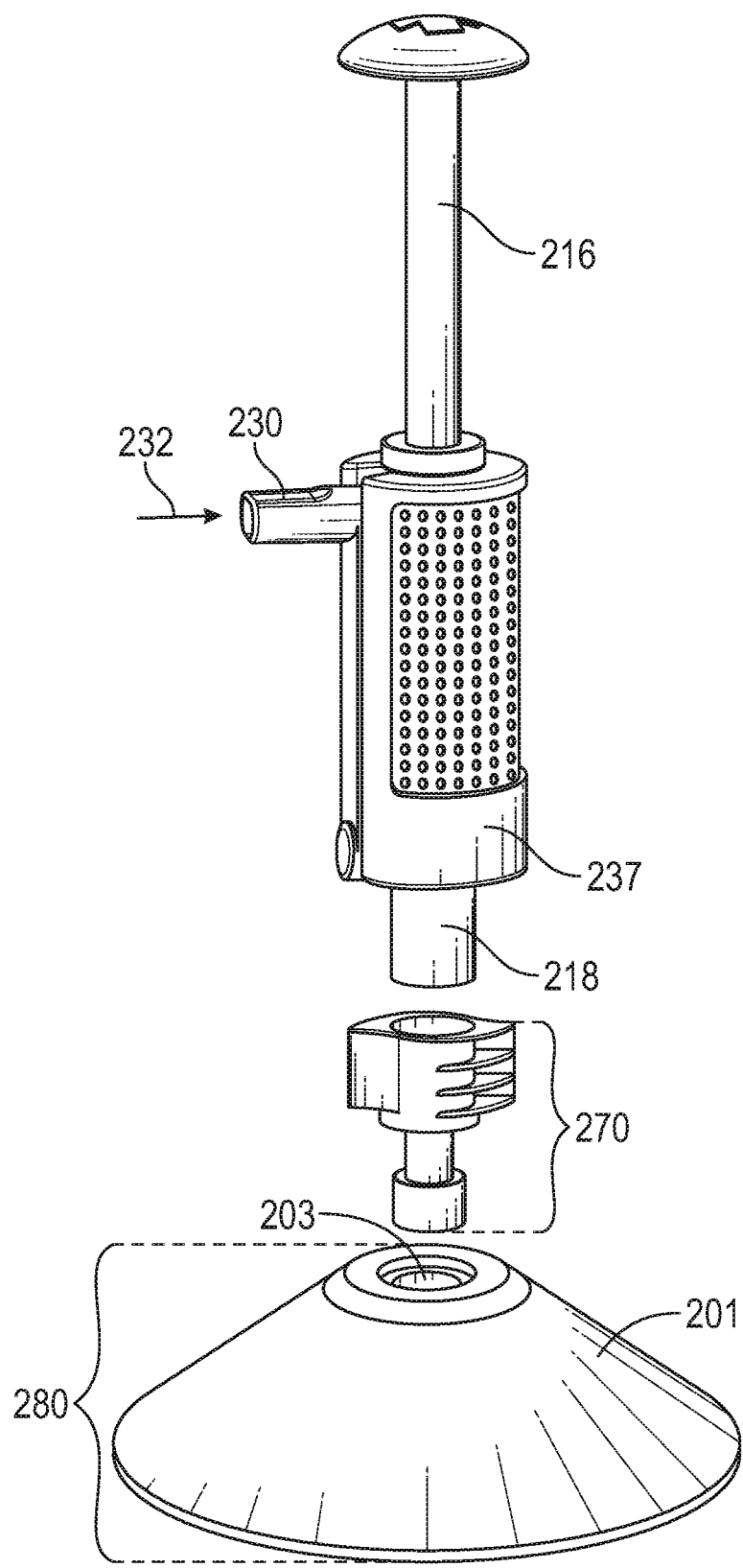

FIG. 2C shows a schematic diagram of an outside view of the collection unit 260, the mixing unit 270 and the receptacle 280. The collection unit 260 includes a mouthpiece 230 and collection chamber 218, which is housed inside a cooling device 237 and contains a plunger 216 at a first end and components that are compatible with a mixing unit 270 at a second end. The mixing unit 270 is compatible with a receptacle 280 containing a baseplate 201. The preferred system showcased herein contains separate components for collection, mixing and detection. In such a disintegrated system, the mixing unit, once used, can be discarded and replaced with a new unit, which ensures reliability. Also, the individual components can be cleaned and/or calibrated with ease.

Figure 2D:
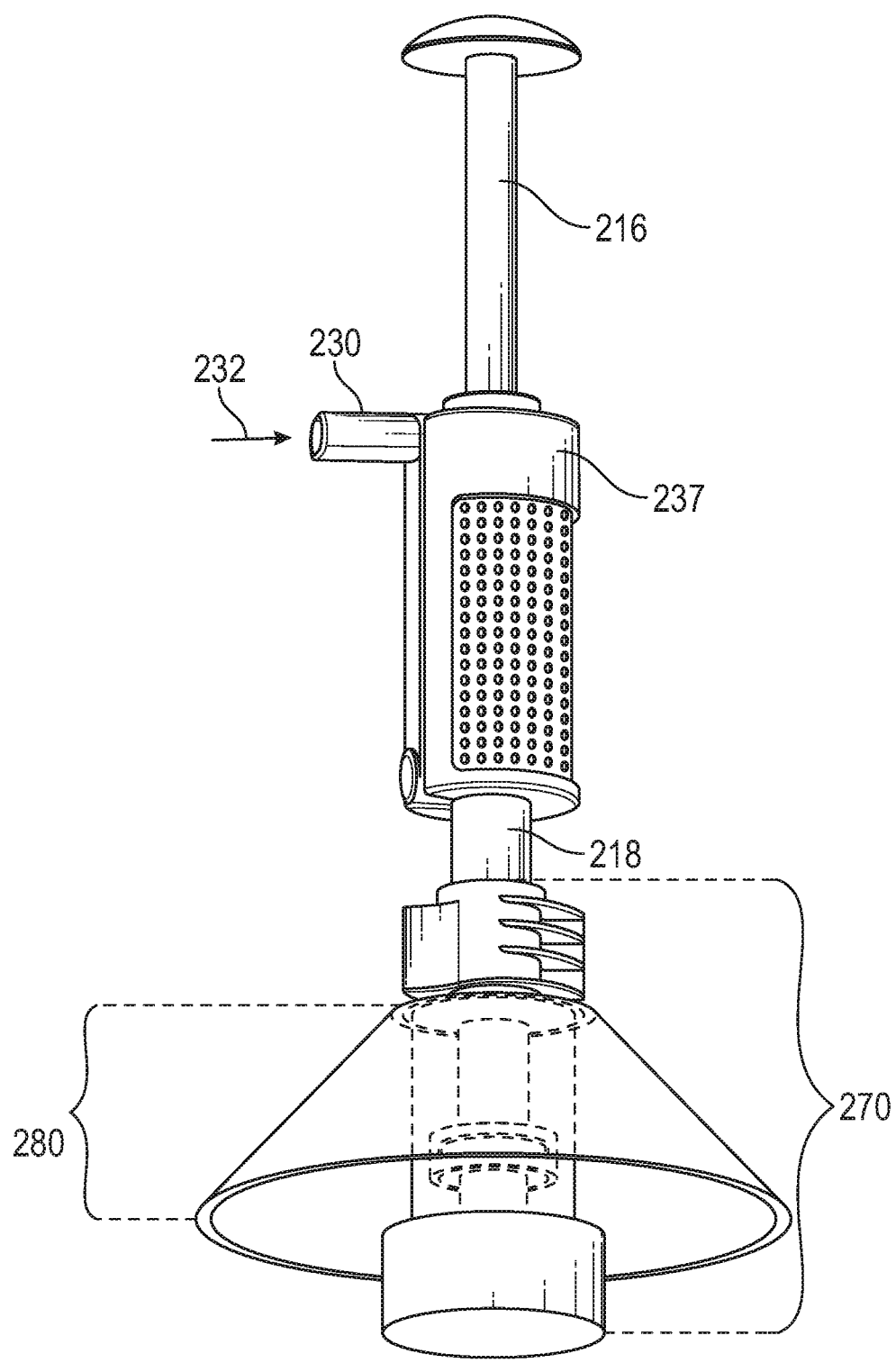

FIG. 2D shows an outer view of the collection unit 260, the mixing unit 270 and part of the receptacle 280 that is engaged with the mixing unit 270, showing how various components of the mixing unit 270 align inside a well of the receptacle. The mixing unit 270 contains a vehicle in a vehicle chamber, which enters an auxiliary chamber via engagement of a plunger and dissolves probes therein to generate an activated probe solution. The activated probe solution generates a signal upon reacting with the EBC marker, which signal that can be detected by a detector in the receptacle 280.

Schematic diagrams of the outer views of the collection unit 218 and the mouthpiece 230. Including various components thereof are shown in FIG. 2E. FIG. 2E-1 shows the collection unit 218 and the mouthpiece 230 in assembled form, wherein the mouthpiece 230 is appended to the shaft of the collection unit 218. FIG. 2E-2 shows the collection unit 218 and the mouthpiece 230 in disassembled form. As shown, the mouthpiece 230 is appended to the shaft of the collection unit 218, precisely at the inlet junction 241 and the outlet junction 242. Inlet valve 239 may be placed at the inlet 241 to control airflow into the collection unit; outlet valve 240 may be placed at the outlet 242 to control airflow out of the collection unit. The mouthpiece end of the collection unit 218 includes a plunger 216, containing a head 243, a linker 244, and a hollow shaft 245 in which a nose 246 may be inserted. Typically, nose 246 is made from a material that provides resistance to outflow of air, e.g., rubber or plastic.

Figure 2H:
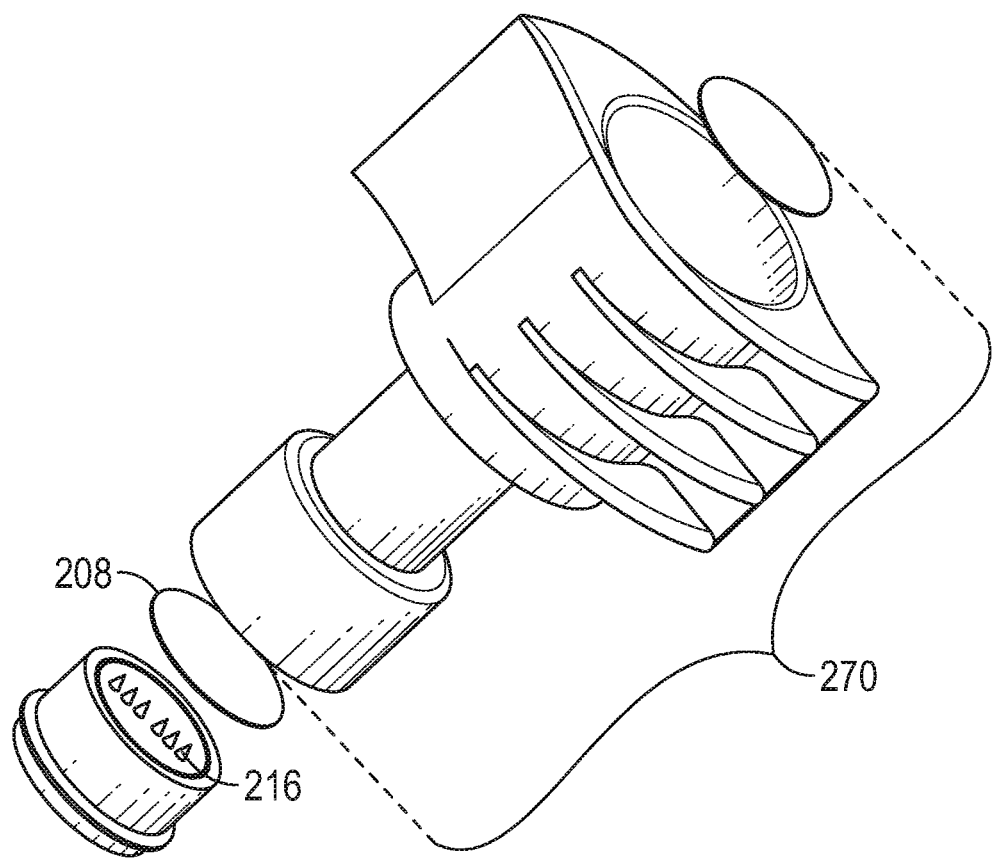

Because many markers in the EBC are volatile and therefore susceptible to temperature fluctuations, the systems of the devices preferably contain cooling units. FIG. 2F shows schematic diagrams of cross-sectional views of the cooling unit 237. FIG. 2F-1 shows a dual-cylinder cooling unit 237 connected to a power source via an inlet 248. FIG. 2F-2 shows a disassembled cooling unit showing the various components such as a lid 249 (to prevent outflow of a coolant), grill 250, shaft 251, cooling plates 252 (to maximize the contact between the EBC and the coolant by providing increased surface area) and base electrical housing 253, which is connected to a power source 248. FIG. 2F-3 shows an assembled view of the cooling unit showing the grill 250, shaft 251, and cooling plates 252.

Preferably, the collection unit 218 and the cooling unit 237 are provided as separate, but compatible components, a representative rendering of which is provided in FIG. 2G. FIG. 2G-1 shows the individual collection unit 218 and the cooling unit 237 in disassembled form. FIG. 2G-2 shows the individual collection unit 218 and the cooling unit 237 in assembled form.

Likewise, the various components that make up the mixing unit 270, may be provided together or separately. In FIG. 2H, the components are provided separately, wherein a component containing the elongated member 216 is separated from the chamber unit of the mixing unit 270 (containing reaction chamber and auxiliary chamber) by a separator 208. These individual units may be purchased separately or together in kit optionally containing instructions for assembly and/or use.

Figure 2I:
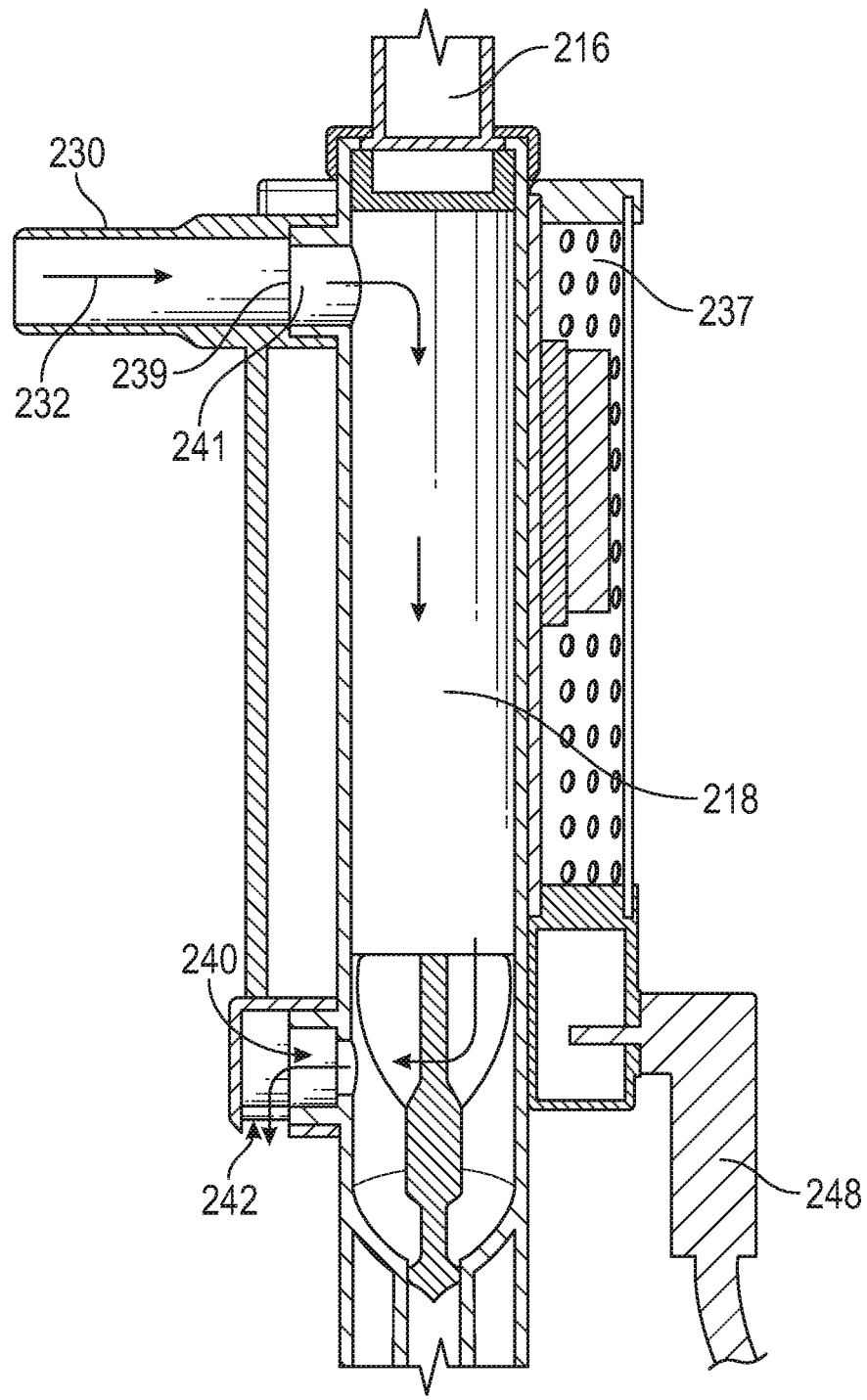
Figure 3A:
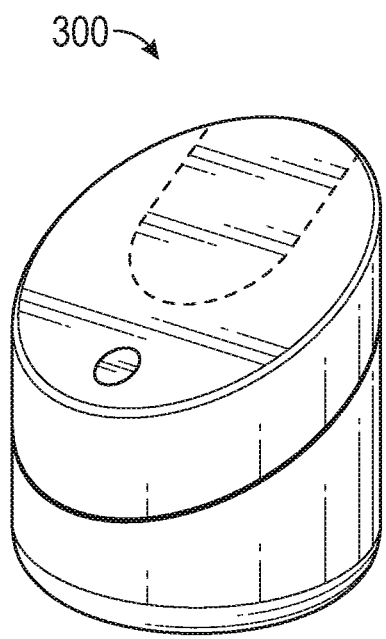
FIGS. 3A-3B shows renderings of the receptacle system 300 for detecting the activated dyes/probes according to exemplary embodiments of the present disclosure.
Figure 3B:
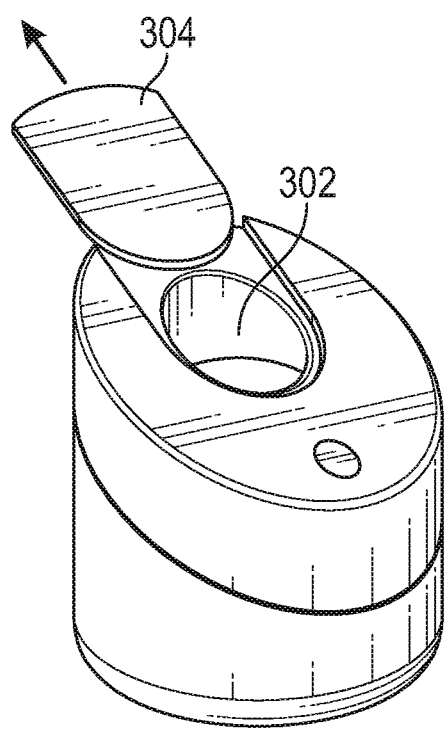

A schematic diagram showing a manner of using an exemplary device of the disclosure is provided in FIG. 2I. EBC 232 is introduced into the collection unit 218 via a mouthpiece 230, the follow of which may be controlled by inlet valve 239. The EBC 232 is forced into the distal end of the collection unit 218 via a plunger 216. The EBC 232 is cooled and the volatile EBC markers therein are stabilized by the cooling device 237, which is powered by a power source 248. The EBC 232 is forced into the mixing unit, where it reacts with the activated probe components (not shown). After measurement is taken, the residual EBC is forced out of the collection unit 218 via an outlet 242. Preferably, the opening of the outlet 242 is controlled by an outlet valve 240, which is normally unresponsive to forced exhale but responsive to a compressed air source (e.g., canned gas containing diflouroethane). This allows the collection unit to be cleaned easily after each use.

Figure 4C:
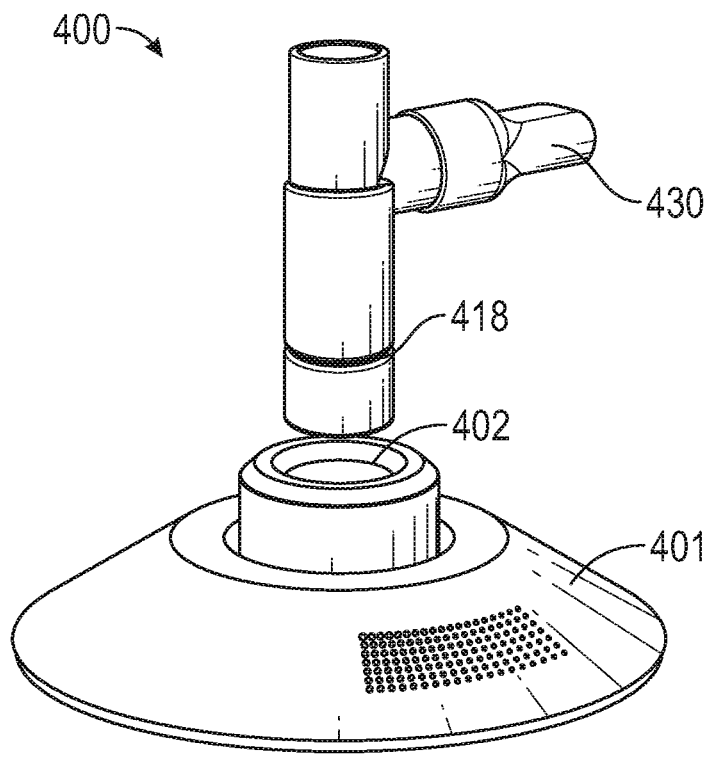
Figure 4D:
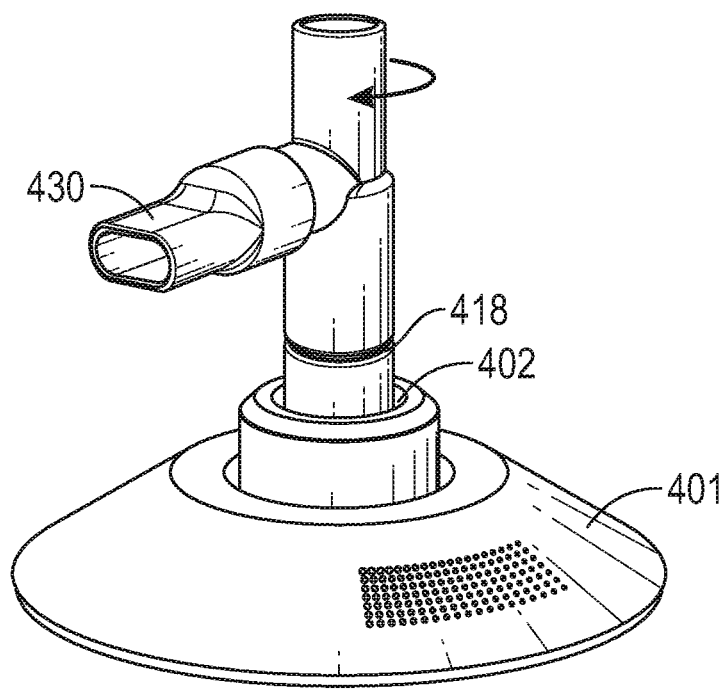
Figure 4E:
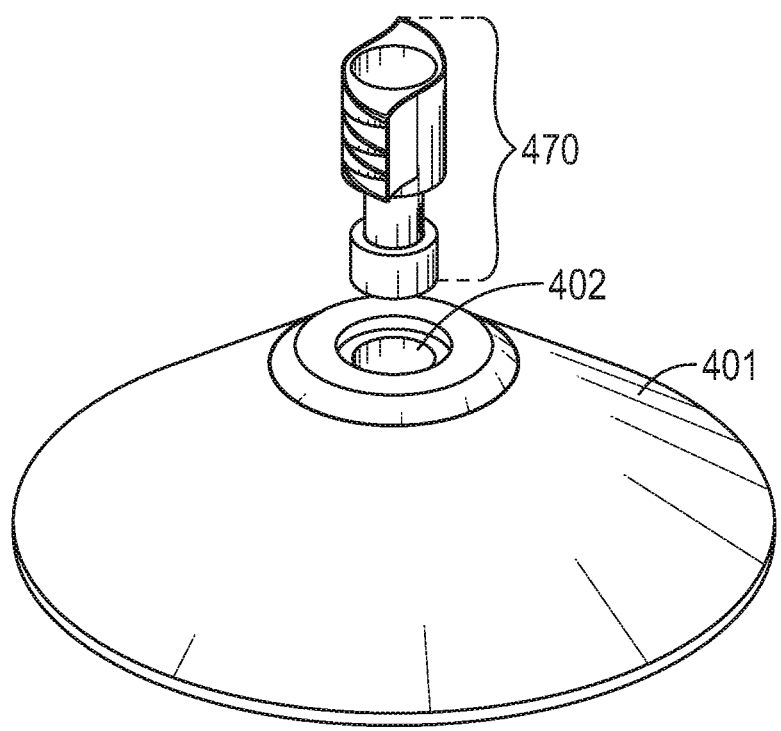

In some embodiments, the EBC marker detection system may further include a receptacle 300 (FIG. 3) that comprises a slidable lid 304 and a housing well 302. In one embodiment, the lid 304 shields the detector from noise, allowing a baseline to be accurately measured (closed position 300). The receptacle 300 optionally contains components for detection, processing and/or transmission of the detected signal to generate readouts, which are viewable to the user on a monitor. In some embodiments, the receptacle (FIG. 3) is compatible with the article, wherein the window 114, 214 of the reaction chamber 120, 220, when inserted into the housing well 302, 402, is aligned with the components for detection of the signal (as shown in FIG. 4). In a related embodiment, the disclosure further provides for portable, battery operated receptacles 500 (FIG. 5) that can be transported conveniently by a user, e.g., clinician.

Figure 7:
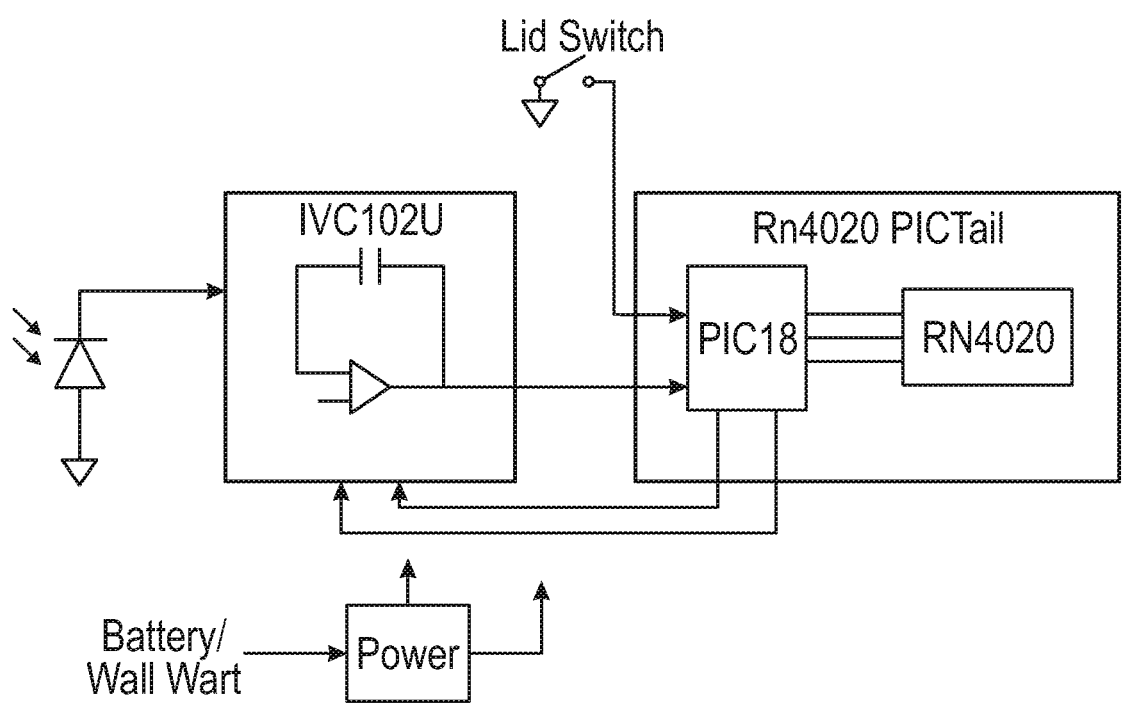
FIG. 7 shows the electrical circuitry of an exemplary sensor used in the analytical device according to exemplary embodiments of the present disclosure.

The articles and/or receptacles of the disclosure may further comprise a plurality of sensors for detection and/or quantification of markers present in the sample. One representative example of the sensor comprising a photodiode is shown in FIG. 7. The sensor is a part of the system architecture, which may include hardware architecture and software architecture, as described below.

The term "sensor," as used herein, includes any technology that can be used to detect and/or measure the concentration or amount of a marker present in EBC (such as $H_2O_2$). Sensing devices for detecting glucose in EBC can include electrochemical devices, optical and chemical devices and combinations thereof. A more detailed description of sensors that can be used in accordance with the present invention is provided below.

Sensors contained in the devices of the disclosure may be direct or indirect. As the name suggests, direct sensors comprise molecules which are capable of reacting with the marker and producing a change, which can be recorded. For example, a direct sensor capable of detecting changes in current as a result of a changing hydrogen peroxide concentration in the EBC may be employed in accordance with the present disclosure. Herein, the sensing element is typically an electrode as used in electrochemical sensors. After uptake and diffusion to the electrode surface, hydrogen peroxide is electrochemically converted resulting in a concentration dependent current signal. Hydrogen peroxide can be both oxidized and reduced at the electrode surface. Hydrogen peroxide is then detected by direct electrochemical conversion at this electrode, which preferably comprises a platinum electrode. Indirect sensors utilize chemicals such as Prussian Blue or enzymes such as peroxidase to enhance selectivity/catalysis, and the products of catalysis are then detected, which is then correlated with hydrogen peroxide levels.

In some embodiments, electrochemical sensors are employed. These sensors measure a change in output voltage of a sensor caused by chemical interaction of the marker with the sensor. Certain electrochemical sensors are based on a transducer principle while others sense changes in potential at the electrode. Yet others are based on semiconductor technology for monitoring charges at the surface of an electrode that has been built up on a metal gate between the "source" and "drain" electrodes. Additional electrochemical sensor devices include amperometric, conductometric, and capacitive sensors. Electrochemical sensors are excellent for detecting low parts-per-million concentrations. They are also rugged, draw little power, linear and do not require significant support electronics or vapor handling (pumps, valves, etc.) They are moderate in cost and small in size. Regardless of the specific electrochemical technique used to measure $H_2O_2$ concentrations in the EBC can be determined based either on its total mass in the sample or on its concentration. If the sample volume can be controlled accurately, then detecting the total quantity of $H_2O_2$ present allows one to calculate its concentration in the original EBC. This can be accomplished, for example, by utilizing cronoamperometry, which measures the total current required to oxidize the $H_2O_2$ by-product to $O_2$, and this can be related to the number of moles of $H_2O_2$ present.

In some embodiments, the sensors may comprise platinized electrode surface (e.g., platinum or gold) for more efficient detection of hydrogen peroxide and/or nanoparticles or microparticles for a possibly more efficient detection of hydrogen peroxide.

Sensors of the disclosure can include commercial devices commonly known as "artificial" or "electronic" noses or tongues. Other sensors for use in accordance with the subject disclosure include, but are not limited to, metal-insulator-metal ensemble (MIME) sensors, cross-reactive optical microsensor arrays, fluorescent polymer films, surface enhanced Raman spectroscopy (SERS), diode lasers, selected ion flow tubes, metal oxide sensors (MOS), bulk acoustic wave (BAW) sensors, calorimetric tubes, infrared spectroscopy, semiconductive gas sensor technology; mass spectrometers, fluorescent spectrophotometers, conductive polymer gas sensor technology; aptamer sensor technology; amplifying fluorescent polymer (AFP) sensor technology; microcantilever technology; molecularly polymeric film technology; surface resonance arrays; microgravimetric sensors; thickness sheer mode sensors; surface acoustic wave gas sensor technology; radio frequency phase shift reagent-free and other similar micromechanical sensors.

In some embodiments, the EBC may be analyzed for markers that are indicative of pH of pulmonary tissue in a subject. Normal range of pH values of fluid lining human airways ranges from about pH 6.5 to about pH 7.5 (Tanaka et al., *Eur. Respir. J.* 11:1301-1306, 1998). Sampling may be accomplished by having a subject breath at tidal volumes orally into a mouthpiece of the present disclosure. In some embodiments, the mouthpiece may be attached to a cold condenser, e.g., RTube, Respiratory Research Inc., Austin, TX, USA; ECOSCREEN II, VIASYS Healthcare, Yorba Linda, CA, USA). In this instance, pH may be assayed after argon de-aeration of the EBC. In addition to oral collection methods, EBC may be collected through a nasal cannula and or an endotracheal tube. Collection times may be as short as 5 seconds or over 20 minutes or more to obtain sufficient EBC. Alternatively, pulmonary pH of a subject may be monitored in real time using a miniaturized self-condensing pH sensor as described by Tsukashima et al. (U.S. Pub. No. 2007/0068810).

The devices disclosed herein may further contain sensors to reduce noise. For instance, some fractions of an exhaled breath can yield different concentrations of certain EBC than other fractions. For example, the first one-third to one-half of an exhaled breath comprises mostly air that has been inhaled into the test subject's upper airway, but never gets into the deep lungs, where gas exchange takes place. Therefore, concentrations of EBCs that originate in the deep lungs are higher in later fractions of the exhaled breath than in earlier fractions. Therefore, for some types of EBCs targeted for detection in carrying out the diagnosis according to the disclosure, it may be desirable to select only the later fractions of the exhaled breaths for collection and to divert earlier fractions away from the collection means or processes. This feature of the disclosure can be implemented in a number of ways, including, but not limited to, detection and use of markers, for example, carbon dioxide concentration, which is also higher in the later fractions of the inhaled breath, to control such flow diversions or to turn collection means and processes on and off. Other representative methods are described in U.S. Pub. No. 2010/0324439.

The collection units used with the systems and methods of the instant disclosure are designed to allow rapid (e.g., lasting less than five minutes, preferably less than 30 seconds, even instantaneous, e.g., less than 5 seconds), noninvasive collection of EBC from a spontaneously breathing subject or a patient receiving mechanical ventilation, followed by one-step quantitative or semi-quantitative analysis of the condensate for the concentration of a marker such as peroxide. In spontaneously breathing subjects, the exhaled condensate may generally be collected via a mouthpiece 230 held by the lips; however, in patients with severe respiratory distress, the sample may be collected by fitting the patient with an airtight, snug-fitting facemask that allows the delivery of oxygen, while allowing the diversion of exhaled gases and EBC into a collection unit such as those described above.

The disclosure further relates to a plurality of cartridges comprising the aforementioned components, wherein each of mouthpiece 230, collection chamber and the tri-chambered analytical article are separable from each other. Preferably, the collection chamber is compatible with the mouthpiece 230 on one end and the tri-chambered article on the other end. For example, in one embodiment, the distal end of the collection unit may form a sealable (e.g., airtight) junction with the reaction chamber of the tri-chambered article. In another embodiment, the collection unit may comprise only the mouthpiece 230 which forms a sealable junction with the reaction chamber. Preferably, the EBC collection unit and analytical units of the disclosure are provided in an assembled unit. FIG. 2 provide a schematic representation of various components of such a unit, which may be provided together so as to eliminate the need for assembly.

Figure 5:
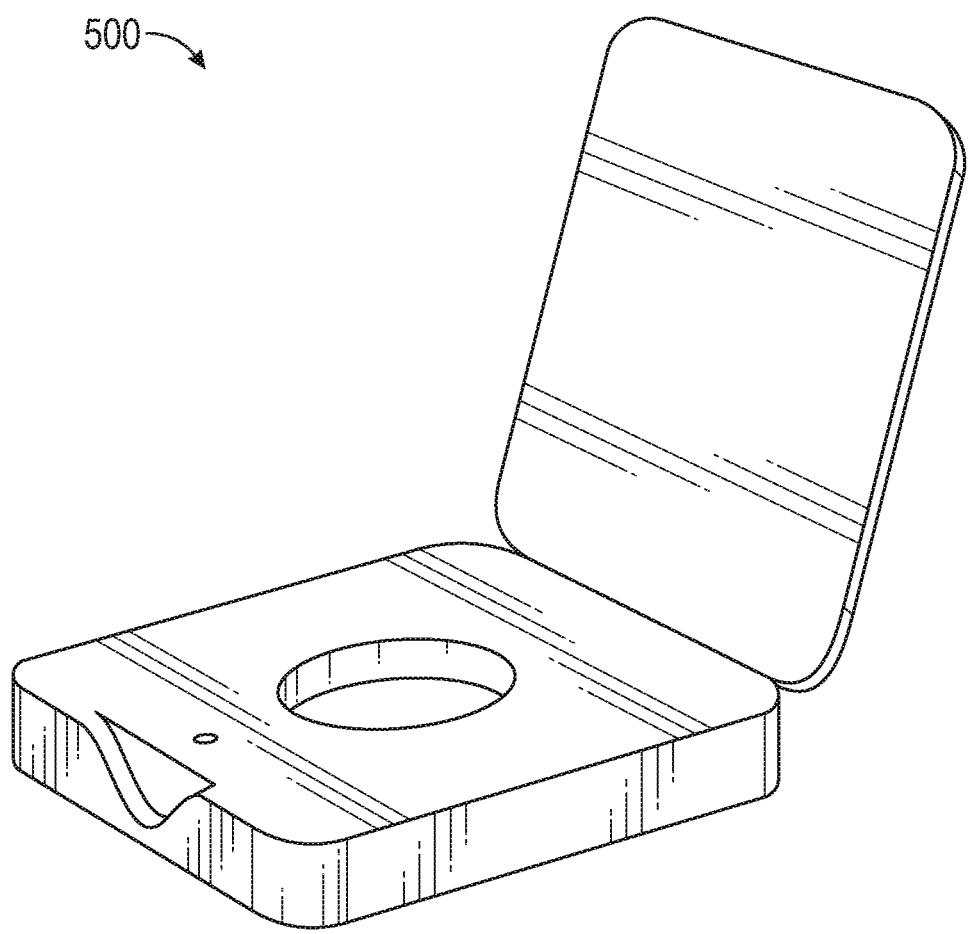
FIG. 5 shows a portable receptacle 500 which can be conveniently transported to and from a testing site according to exemplary embodiments of the present disclosure. This unit is battery operated and optionally comprises fasteners at the bottom end (opposite to the lid 304 and the latch, as shown in FIG. 3B).

The disclosure further relates to receptacles that are capable of receiving the aforementioned articles and/or devices. FIG. 3 is a perspective view of a measurement device capable of receiving a breath collection device and taking a photometric reading (measurement) of a reagent that has been exposed to a breath sample. As shown in FIG. 3, sample receiving door can be opened (e.g., by moving the door laterally) to reveal a sample receiving area. When the door is in the open position (FIG. 3 and FIG. 4), a sample (e.g., a breath collection device containing the analytical unit that has been exposed to an exhaled breath condensate) can be inserted into the receiving area. In the illustrated embodiment (FIG. 4), a device comprising, e.g., a reader and a baseplate, includes a cover and a housing well 402. The device can be powered by a power source such as battery (e.g., rechargeable battery), which can be received in a lower portion of the bottom member. FIG. 5 provides an exemplary battery powered receptacle, comprising, e.g., a reader and a baseplate, that can be transported easily, e.g., via use of appropriate adapters such as belt-buckles. The receptacle may comprise cables and units for charging and an LED screen to display charge status. If a direct power-source is implemented, voltage and forward current from the power source is preferably controlled to minimize variations in LED strength during testing conditions.

As indicated in FIG. 4, the receptacle is preferably compatible with the article. The sample receiving area is defined by a housing well 402 and a sliding lid 404. The lid 404 is movable relative to the receptacle. The cover may be fastened using appropriate fasteners. To load a sample into the well 402, the detection chamber end of the analytical unit is pushed into the well 402 until a transparent window 114 or transparent base in the detection chamber engages with the reader in the receptacle (not shown). A downward force can be directed at the top of the collection unit causing the system to move downward together until it latches into the receptacle. To ensure proper topological orientation of the collection unit (male) in the receptacle (female), appropriate markers and/or ridges may be used to insert the article into the measurement device. A latch may also be used to secure the collection unit in place. To ensure that the collection unit has been appropriately positioned within the receptacle, the device can also include a switch that is movable between a first position and a second position.

The measurement devices further include a light measurement system (LMS) positioned adjacent a window 114 on the reaction chamber. The light measurement system may include a light emitting device (LED) and one or more light sensing devices (e.g., photometers). The light measurement system can also define a light pathway between the light emitting device(s) and the light sensing device(s). The window 114 provides access to the product of the reaction between the marker and the probe 110 so that the product can be exposed to light emitted from the LED of the LMS.

Since the presence of undissolved reagents or other contaminants in the reaction chamber can interfere with the light emitted and received by the LMS, the contaminants are preferably substantially prevented from entering the measurement area, e.g., via use of meshes, gauzes, etc. Moreover, since the detection chamber is oriented at the top while the vehicle chamber 102 is oriented at the base, any undissolved reagent particles to settle on a mesh barrier to prevent particulate matter from settling on the bottom of the chamber where the sensor would be aimed in the vehicle chamber 102 and likely not interfere with the measurement.

The LED and the photometer can be coupled to one or more circuit boards, a representative example of which is shown the block diagram of FIG. 7. While the various components described herein are merely illustrative, one skilled in the art can, using the specific components and architectures described herein, design a working system that is implementable with the devices of the disclosure.

Exemplary hardware architecture of the device is shown the block diagram of FIG. 7. A photodiode is connected to a precision integrating amplifier with FET op amp, integrating capacitors, and low leakage FET switches (e.g., IVC102U from Texas Instruments, Richardson, TX). This transimpedance amplifier device integrates several of the discrete components for the integrating amplifier into an integrated circuit. The IVC102U reset and hold switches are controlled from otherwise unused general-purpose input/outputs (GPIO) from a microcontroller (e.g., PIC18) on the communication module (e.g., RN4020 bluetooth module, Microchip Technology Inc., Chandler, AZ) that is coupled to a compatible board (e.g., PICTAIL board, Microchip Technology, Inc.). The analog output from the transimpedance amplifier (IVC102U) is fed to one of the unused GPIO analog A/D converter inputs on the microcontroller (e.g., PIC18). The switch that detects the closing of the enclosure lid 304, 404 (see, FIG. 4) is also connected to an unused GPIO. A power supply section can be used to generate the different supply levels needed for the circuitry.

The software running in the microcontroller (e.g., PIC18) on the compatible board (RN4020 PICAIL board) is responsible for controlling the entire embedded system. Although both direct current and alternating current may be used, the device is preferably powered from an AC source so low power operation is not required.

With regard to the software architecture, routine programming may be used to run and test the assembled hardware architecture. Without being bound to a particular embodiment, an exemplary software architecture of the device is described below. The following glossary provides short descriptors of the components used in software architecture:

"Measurement store" may include a storage area that holds at least 3 measurements.

"Measurement" may include a 30 second set of samples.

"Sample time" may include the period between recorded samples. This will depend on the available memory. It is required to be 500 mS or less.

"Sample" may include an accumulation of multiple sub-samples.

"Sub-Sample" may include the sample from the A/D converter which is a record of the integrating amplifier output.

"Sub-Sample time" may include the time the hardware integrating amplifier is integrating.

The system operation comprises steps of initialization, which includes performing the following functions: initialization of the Bluetooth module and setting it to discoverable mode; and initialization of interrupt vectors and configuration for interrupts on events such as Bluetooth event, lid switch opened or closed, sub-sample timer expiry event, watchdog interrupt, etc. Next, the signals controlling the measurement circuit are initialized. Next, the internal data structures and measurement stores are initialized. Next, the LEDs are initialized to indicate that the device is on, or not connected and/or not measuring. If all these initialization steps are successfully performed, the CPU enters the idle state waiting for an event.

The following output are provided: (1) for the application functionality, including e.g., connection to Bluetooth devices, depending on the type of function, the following output is provided: connected (record that the device is now connected, which results in a change in LED status) or disconnected (indicating that the device is no longer connected, which also results in a change in the LED status). (2) For receipt of packets, when a valid packet is received, and a request for measurement is made, if measurements store is not empty, the transmission of oldest stored measurement is initiated. If measurement store is empty, a message that no measurements are present is provided. Additionally, if a request for the deletion of measurements is made then the oldest stored measurements are deleted or an error is provided, wherein there are no measurements stored. (3) For opening and/or closure of lids, if a measurement is in progress while the lid 304 is open, the sampling is terminated and the collected data is deleted. The LED indicating a measurement is in progress is turned off. When the lid 304 is closed and measurement is initiated the sub-sample timer interrupt is initiated, measurement is started, and the LED is activated to indicate that a measurement is being performed. If during measurement, the measurement store is full, the oldest measurement is removed to make room for the new data. (4) For dispensing timer events, when this timer expires, a hold on the integrating amplifier is performed, the A/D result is read, and a reset is performed, followed by a hold release on the integrating amplifier. Additionally, if enough subsamples have been accumulated for a sample, the sample is recorded in the measurement store. Once enough samples have been recorded (over a specified duration, e.g., 30 sec, 60 sec, etc.), then the measurement is completed. The system records that a measurement is now ready in the measurement store. However, if not enough samples have been collected yet, then the sub-sample timer interrupt is initiated again and the LED may be triggered to indicate that the measurement has stopped.

Preferably, in order to shield the sample from ambient light (which overexposes the sensor during the measurement) special care may be applied to ensure that the tests are conducted in an appropriate environment (e.g., darkroom) and the opening and closing of the lid 304 is particularly monitored. Additionally, special attention may be needed in the mechanical placement, signal layout, ground/power supply distribution, decoupling and digital/analog noise isolation, which may be achieved by carefully designing and implementing the analog integrating amplifier circuit. This may be accomplished using one or more light management systems (LMS).

After the LMS takes one or more measurements, an algorithm can be used to generate a quantitative "score" reflective of the amount of markers, e.g., peroxide, detected by the device. If desired, a qualitative "red/green" indicator can be used to identify the quantity of markers, e.g., peroxide, in the breath. However, a numerical "score" is preferred so that the amount of markers, e.g., peroxide, detected by the device can be more accurately identified. The range of the "score" can be selected based on the accuracy with which the substance being measured can be identified. In most cases, a range of 1-100 or 1-1000 is sufficient.

The LED emission spectrum and photometer response spectrum can be selected based on the particular chemistry to be measured. Thus, for example, if desired, an LED that emits a relatively narrow spectrum of light can be used to direct a specific wavelength of light at an exposed reagent. Alternatively, an LED can be selected that delivers a broader spectrum of light (e.g., a white light) at the exposed reagent. Similarly, different photometers can be selected depending on the breadth of the spectrum of light that is relevant to the colorimetric reaction that is to be measured.

In certain embodiments, a plurality of LEDs comprising, e.g., a first and a second LED, can be used to emit the same spectrum of light or they can be used to emit different spectrums of light. If the first and second LEDs are configured to emit the same spectrum of light, the amount of light emitted at the exposed reagent is doubled, providing a greater amount of reflected light that can be measured by the photometer. In other embodiments, however, it may be desirable to configure the first LED to emit a first spectrum of light and the second LED to emit a second spectrum of light that is different from the first spectrum of light. Thus, the first and second LEDs can measure the colorimetric reactivity of a reagent at two different spectrum regions.

Various wavelength filters can be used in connection with the devices disclosed herein. For example, the effective wavelength(s) that the photometer system measures can be modified as needed by the addition of wide band optical filters on either the emitting (LED) side and/or the receiving (photometer) side of the system. Thus, if desired, the infrared (UV) range from 620 nm to longer wavelengths and the ultraviolet range from approximately 350 nm and shorter wavelengths can be restricted using a wavelength filter. Additionally, narrow band optical filters can be used to limit noise and optimize the signal generated via the reaction between the marker and the probe 110.

The disclosure further relates to interactive modules comprising the articles, devices, and systems described hereinbefore. In one embodiment, the interactive module comprises an application ("app") for an interactive device, e.g., a smartphone, a tablet, a computer, or the like. The data, either raw or in processed form, which is collected by the articles, devices, and systems, is fed into the interactive device via direct or indirect connection (e.g., via a cable or wirelessly such as Wi-Fi or Bluetooth connection). The application initiates the test and the user-interface therein provides information to the user. In certain embodiments, based on a history, the app may also provide personalized treatment, e.g., monitoring of dose of therapeutic drugs, dietary changes, lifestyle changes, and the like. The app may also track symptoms or patterns of occurrence and correlate with the marker levels. The app may further enable a user to schedule checkups or undergo further diagnostic tests to validate the recorded history in the app. In a particular embodiment, provided herein are mobile applications in standard operating systems (e.g., IOS or ANDROID) that connect to the standalone articles, devices and/or systems through a connection (e.g. wireless or Bluetooth connection) and allows users to interact with the device in order to track and view results, and connect users with globally collected data.

The disclosure further relates to kits for diagnosing pulmonary diseases, e.g., asthma, COPD, IPF, CF, etc., comprising, in one or more packages, an analytical unit comprising the vehicle chamber 102, the auxiliary chamber and the reaction chamber; and instructions for assembling and/or using the analytical unit. The kit may optionally comprise a collection unit comprising a mouthpiece 230 and the collection chamber. Further optionally, the kits may comprise a marker standards in different concentrations as a means of calibrating the analytical and/or detection units for guiding the diagnosis based on the analytical technique preferably involving luminescence, and a manual as a means of indicating content ranges of the marker for diagnosing the severity of the pulmonary disease in view of the content of the marker detected.

The disclosure further relates to methods for making the articles, systems and devices of the disclosure. In one embodiment, the method includes providing a three-chambered article, comprising a central auxiliary chamber and terminal vehicle chamber 102 and reaction chamber, wherein the auxiliary chamber is connected to the vehicle chamber 102 on one end and a reaction chamber at the second end. The various components of the reaction chamber, e.g., the reaction surface 124, the elongated member(s), 126 and the X4 chip, optionally together with other components such as sensors, may be assembled prior to manufacture of the device. In another embodiment, a system comprising a plurality of plungers allowing dispensing of the contents of one chamber into the other via initiation of the plungers, either sequentially or in unison, may be provided. Such a system may be custom manufactured using routine techniques. The aforementioned components of the reaction chamber may be embedded or incorporated into the assembled system using etching or printing techniques known in the art.

Once the housing of the article is provided, the auxiliary chamber is filled with the probe 110 comprising, e.g., the dye (D), the reactive chemical (C) and optionally a catalyst (K)

and other polymers (P) at an amount effective to detect marker levels, e.g., peroxide levels, in an EBC sample of a subject, e.g., an asthmatic human subject. The auxiliary chamber is then sealed from the vehicle chamber 102 and the reaction chamber with a plurality of breakable separators. The vehicle chamber 102 is loaded with an appropriate vehicle 104 and capped to prevent leakage. A collection unit comprising a mouthpiece 230 is mounted onto an open end of the reaction chamber (e.g., the end that is not connected to the auxiliary chamber). The reaction chamber may further be fitted with a plurality of components to optimize collection, performance, and/or functionality of the system.

The disclosure further relates to methods for the diagnosis of pulmonary diseases. Pulmonary diseases are extremely common in the general population, and more so in certain ethnic groups, such as African Americans. In some cases they are accompanied by inflammation, which aggravates the condition of the lungs. Diseases such as chronic obstructive pulmonary disease (COPD), asthma, allergic rhinitis, cystic fibrosis, and acute respiratory distress syndrome (ARDS), including RDS in pregnant mothers and in premature born infants, among others, are common diseases in industrialized countries, and in the United States alone, they account for extremely high health care costs. These diseases have recently been increasing at an alarming rate, both in terms of prevalence, morbidity and mortality. In spite of this, their underlying causes still remain poorly diagnosed.

As used herein, the term "diagnosis" refers to methods by which a determination can be made as to whether a subject is likely to be suffering from a given disease or condition, including, but not limited to, diagnosis of diseases or conditions characterized by pulmonary conditions. In some embodiments, diagnosis is carried out by monitoring or examining the subjects for characteristics or traits, including, assisting in the monitoring or examination. The skilled artisan often makes a diagnosis on the basis of one or more diagnostic indicators, e.g., a marker, the presence, absence, amount, or change in amount of which is indicative of the presence, severity, or absence of the disease or condition. Other diagnostic indicators can include patient history; physical symptoms, e.g., shortness of breath. A skilled artisan will understand that the term "diagnosis" refers to an increased probability that certain course or outcome will occur; that is, that a course or outcome is more likely to occur in a patient exhibiting a given characteristic, e.g., the presence or level of a diagnostic indicator, when compared to individuals not exhibiting the characteristic. Diagnostic methods of the disclosure can be used independently, or in combination with other diagnosing methods, to determine whether a course or outcome is more likely to occur in a patient exhibiting a given characteristic.

Accordingly, the disclosure relates to diagnosis of pulmonary diseases such as asthma, cystic fibrosis, idiopathic pulmonary disease, via detection of a marker associated therewith, using the article, devices, and systems disclosed herein. In one embodiment, the marker is hydrogen peroxide or a derivative thereof, e.g., peroxide anion ($O_2^{-2}$) or a peroxide radical ($^{\cdot}OH$).

In some embodiments, a method for detecting an EBC marker is provided. The method includes providing the EBC marker detection system comprising the article (FIG. 1 and FIG. 2) described above, initiating the first plunger 212 to disengage the first separator 208, thereby allowing the vehicle 204 in the vehicle chamber 202 to enter the auxiliary chamber 206 and dissolve the probe 210 to generate an activated probe solution; collecting an EBC sample 232 from a subject via exhalation into a mouthpiece 230 connected to the reaction chamber 214; initiating the second plunger 216 to disengage the second separator 222, thereby allowing the activated probe solution to enter the reaction chamber 220 and react with the EBC marker on a surface 224 to generate a signal; and detecting the signal. In some embodiments, the second plunger 216 may also assist in pushing the EBC sample into the reaction chamber 214, thereby improving the speed and sensitivity of the detection. In some embodiments of the articles of the disclosure, a semi-disposable reaction chamber 220 comprising a sensor, as described above, is fitted with a reagent storage chamber in a manner such that, following a test, the reaction chamber may be cleaned and the reagent storage chamber may be replaced. Such a semi-disposable unit would eliminate potential waste and also save costs associated with a fully disposable reaction chamber.

In one embodiment, the signal is a chemiluminescent signal which can be detected via a sensor. In embodiments of the device containing the microfluidic chips, the sensor may be coupled to a microfluidic chip, for example, by placing them in close proximity to each other on the reaction surface 224. In one embodiment, the marker is an oxidative marker such as $H_2O_2$.

In another embodiment, a plurality of markers may be detected to practice the diagnostic methods. For instance, in one embodiment, the disclosure relates to a method comprising detection of a plurality of markers comprising a first marker which is hydrogen peroxide or a derivative thereof and a second marker selected from hydrogen ions ($H^+$), malondialdehyde, 8-isoprostanes, thiobarbituric acid reactive substances (TBARS), acetone, nitrosothiols, and nitric oxide-derived products.

In one embodiment, the disclosure relates to diagnosis of asthma. Management of asthma patients is especially problematic given that nearly 28% of all subjects are misdiagnosed and nearly 55% of the patients have uncontrolled symptoms; and nearly 25% of all subjects are under unnecessary medications. See, Pakhale et al., *BMC Pulm Med.*, 11: 27, 2011; Peters et al., *J Allergy Clin Immunol.*, 119(6): 1454-61, 2007; Powell et al., *Lancet* 10; 378(9795):983-90, 2011; and Syk et al., *J Allergy Clin Immunol Pract.*, 1(6): 639-48, 2013. According to the Central for Disease Control (CDC) report in 2011, direct treatment and indirect patient costs for asthma rose from $53B in 2002 to $56B in 2007 in the U.S. alone. It is estimated that currently, uncontrolled asthma costs $195.4 billion annually, while controlled asthma costs $72.6 billion annually.

Asthma is a condition characterized by variable, in many instances reversible obstruction of the airways. This process is associated with lung inflammation and in some cases lung allergies. Many patients have acute episodes referred to as "asthma attacks," while others are afflicted with a chronic condition. The asthmatic process may be triggered in some cases by inhalation of antigens by hypersensitive subjects. This condition is generally referred to as "extrinsic asthma." Other asthmatics have an intrinsic predisposition to the condition, which is thus referred to as "intrinsic asthma," and it encompasses conditions of different origin, including those mediated by the adenosine receptor(s), allergic conditions mediated by an immune IgE-mediated response, and others. Asthma is characterized with its associated symptoms: bronchoconstriction, lung inflammation and/or decreased lung surfactant. However, diagnosis and prognosis of asthma remains particularly poor. The most recognized way to diagnose asthma is with a lung function test, a medical history, and a physical exam. However, it's hard to do lung function tests in children younger than 5 years.

Thus, doctors must rely on children's medical histories, signs and symptoms, and physical exams to make a diagnosis. Other tests may include allergy testing to identify the causative allergens; broncho-provocation test for measuring airway sensitivity; chest X ray or an EKG (electrocardiogram). Despite improvements in diagnostic methods, the commonalities of symptoms of asthma and other unrelated diseases such as reflux disease, vocal cord dysfunction, and/or sleep apnea complicates the diagnostic process. Misdiagnosis and/or failed diagnostic is common. Doctors commonly use a 4-6 week trial of asthma medicines to see how well a patient responds prior to determining the idiopathic cause of the symptoms presented.

The disclosure relates to diagnosis of all forms of asthma, including, controlled and uncontrolled asthma. Given that studies indicate that the lung tissues of patients suffering from uncontrolled asthma are in an elevated oxidative stress (as demonstrated by significantly higher peroxide levels in EBC; see Teng et al., supra), it is believed that the articles, devices and systems of the disclosure will be particularly useful for the diagnosis of uncontrolled asthma.

In one embodiment, the disclosure relates to methods for the diagnosis of general asthma. For instance, compared to controls (e.g., healthy subjects), an elevation in the level of EBC $H_2O_2$ between about 0.05 µM to about 20 µM, specifically about 0.2 µM to about 10 µM (particularly between about 0.4 µM to about 2 µM); and especially about 0.5 µM) indicates that a subject is suffering from general asthma. In another embodiment, the disclosure relates to diagnosis of intermittent, mild to moderate persistent, or severe asthma. For instance, compared to controls (e.g., healthy subjects), an elevation in the level of EBC $H_2O_2$ of about 0.53 µM (range about 0.5 µM to about 0.6 µM) indicates that a subject is suffering from intermittent asthma. Similarly, an elevation in the level of EBC $H_2O_2$ of about 0.62 µM (range about 0.6 µM to about 1.0 µM) indicates that a subject is suffering from moderate asthma; an elevation in the level of EBC $H_2O_2$ of about 1.3 µM (range about 1 µM to about 2 µM) indicates that a subject is suffering from severe asthma. As is known in the art, these measurements may vary depending on the type and sensitivity of the instrumentation used and may deviate by, e.g., as much as 80%, but particularly less than 50%, or especially less than 20%, or less than 10% from the stated numerical value.

In yet another embodiment, the disclosure relates to methods for the diagnosis of controlled or uncontrolled asthma. For instance, in human subjects, compared to controls (e.g., healthy subjects) an elevation in the level of EBC $H_2O_2$ between about 0.5 µM to about 1.1 µM (particularly about 1.06 µM) indicates that the subject is suffering from controlled asthma and an elevation in the level of EBC $H_2O_2$ between about 1.1 µM to about 1.5 µM (particularly about 1.37 µM) indicates that the subject is suffering from uncontrolled asthma.

In yet another embodiment, the disclosure relates to methods for the diagnosis of drug-responsive and drug-nonresponsive asthma subjects. An example of an anti-asthma drug is a steroid. For instance, compared to a control subject (e.g., steroid responsive human subject taking a steroid), if the level of EBC $H_2O_2$ is elevated by about 0.1 µM to about 0.5 µM (particularly about 0.19 µM) in an experimental subject (e.g., a subject whose responsiveness to steroid therapy is to be monitored), it is indicative that the experimental subject is not responsive to drug treatment.

In another embodiment, the disclosure relates to diagnosis of COPD. COPD is characterized by airflow obstruction that is generally caused by chronic bronchitis, emphysema, or both. Emphysema is characterized by abnormal permanent enlargement of the air spaces distal to the terminal bronchioles, accompanied by destruction of their walls and without obvious fibrosis. Chronic bronchitis is characterized by chronic cough, mucus production, or both, for at least three months for at least two successive years where other causes of chronic cough have been excluded. COPD characteristically affects middle aged and elderly people, and is one of the leading causes of morbidity and mortality worldwide. In the United States it affects about 14 million people and is the fourth leading cause of death, and both morbidity and mortality, have risen, for example, in the United States by 41% since 1982, and the age-adjusted death rates by 71% between 1966 and 1985. This contrasts with a decline over the same period in age-adjusted mortality from all causes (22%), and from cardiovascular diseases (45%). COPD, however, is preventable, given that its main cause is thought to be exposure to cigarette smoke. The disease is rare in lifetime non-smokers. Other proposed etiological factors include airway hyper-responsiveness or hypersensitivity, ambient air pollution, and allergy. The airflow obstruction in COPD is usually progressive in people who continue to smoke, and results in early disability and shortened survival time. Amongst the currently available treatments for COPD, short-term benefits, but not long term effects, were observed with anti-cholinergic drugs, β2 adrenergic agonists, and oral steroids.

In still another embodiment, the disclosure relates to diagnosis of cystic fibrosis (CF). CF (also known as mucoviodosis, or mucoviscidosis) is a genetic disorder known to be an inherited disease of the secretory glands, including the glands that make mucus and sweat. The hallmarks of cystic fibrosis are salty tasting skin, appetite but poor growth and poor weight gain, excess mucus production, and coughing/shortness of breath. Males can be infertile due to the condition congenital bilateral absence of the vas deferens. Often, symptoms of CF appear in infancy and childhood. Although technically a rare disease, cystic fibrosis is ranked as one of the most widespread life-shortening genetic diseases. It is most common among nations in the Western world; one in twenty-two people of Mediterranean descent is a carrier of one gene for CF, making it the most common genetic disease in these populations. In the United States, 1 in 4,000 children are born with CF. In 1997, about 1 in 3,300 Caucasian children in the United States was born with cystic fibrosis. Cystic fibrosis occurs when there is a mutation in the CFTR gene and the loss of functionality thereof resulting in electrolyte (sodium chloride) loss in glandular secretions. This lost salt forms the basis for a sweat test. (Rowe et al., *N Engl J Med.* 352(19):1992-2001, 2005). Cystic fibrosis may be diagnosed by many different categories of testing including those such as, newborn screening, sweat testing, or genetic testing (Stern et al., *N Engl J Med* 336:487, 1997). As of 2006 in the United States, 10 percent of cases are diagnosed shortly after birth as part of newborn screening programs. The newborn screen initially measures for raised blood concentration of immunoreactive trypsinogen. (Davies et al., *BMJ,* 335(7632):1255-59, 2007). Infants with an abnormal newborn screen need a sweat test in order to confirm the CF diagnosis. Trypsinogen levels can be increased in individuals who have a single mutated copy of the CFTR gene (carriers) or, in rare instances, even in individuals with two normal copies of CFTR gene. Due to false positives, CF screening in newborns is somewhat controversial. As such, most states and countries do not screen for CF routinely at birth. The most commonly used form of testing is the sweat test. X-rays and CAT scans are used to examine the lungs for signs of damage or infection. Examination of the sputum under a microscope is used to identify which bacteria are causing infection so that effective antibiotics can be given. Pulmonary function tests measure how well the lungs are functioning, and are used to measure the need for and response to antibiotic therapy. Blood tests can identify liver abnormalities, vitamin deficiencies, and the onset of diabetes. DEXA scans can screen for osteoporosis and testing for fecal elastase can help diagnose insufficient digestive enzymes. Because not all known mutations are found on current tests, a negative screen does not guarantee that a person will not have CF (Tabor et al., *Lancet* 1 (8493):1287-93, 1986). During pregnancy, testing can be performed on the placenta (chorionic villus sampling) or the fluid around the fetus (amniocentesis). However, chorionic villus sampling has a risk of fetal death of 1 in 100 and amniocentesis of 1 in 200 (Tabor et al., supra) in some populations (revised to about 1 in 1600 (Hytonen et al., *Acta Oto-laryngologica*, 121 (8): 945-7, 2001)). Accordingly, prior to CF testing of fetuses, the benefits must be determined to outweigh these risks.

There has been an increasing interest in non-invasive assessment of airway inflammation and oxidative stress in the aforementioned pulmonary diseases. The collection of broncho-alveolar lavage fluid or lung biopsies is invasive, and therefore cannot be applied very easily in children. Non-invasive techniques include measurement of non-volatile inflammatory markers in exhaled breath condensate, and measurement of volatile inflammatory markers in exhaled breath. Fractional exhaled nitric oxide (FeNO), carbon monoxide (CO), ethane and pentane are the most studied volatile markers for CF. See, Paredi et al. (*Am J Respir Crit Care Med* 162:1450-1454, 2000) and Horvath et al. (*Eur Respir J* 18:420-430, 2001). FeNO is most standardized in pathological diagnosing CF (American Thoracic Society (ATS)/European Respiratory Society (ERS) Recommendation in *Am J Respir Crit Care Med*, 171:912-930, 2005). However, there are reports that FeNO may not be a reliable marker for asthma (Teng et al., supra). A follow-up study of 12 specific VOCs by means of a customized gas chromatograph in CF patients and controls identified that dimethyl sulphide (DMS) is significantly lower level in CF compared to controls (Barker et al., *Eur Respir J* 27:929-936, 2006). However, in this study only allows conclusions on a group level; no individual classification of subjects was performed. Insofar as airway inflammation plays a central role in the pathophysiology of CF, the present disclosure also provides devices and systems for monitoring CF markers such as peroxide, which are useful in the clinical diagnosis of CF non-invasively.

In another embodiment, the disclosure relates to the diagnosis of Acute Respiratory Distress Syndrome (ARDS). ARDS (also known as stiff lung, shock lung, pump lung and congestive atelectasis) is believed to be caused by fluid accumulation within the lung which, in turn, causes the lung to stiffen. The condition is triggered within 48 hours by a variety of processes that injure the lungs such as trauma, head injury, shock, sepsis, multiple blood transfusions, medications, pulmonary embolism, severe pneumonia, smoke inhalation, radiation, high altitude, near drowning, and others. In general, ARDS occurs as a medical emergency and may be caused by other conditions that directly or indirectly cause the blood vessels to "leak" fluid into the lungs. In ARDS, the ability of the lungs to expand is severely decreased and produces extensive damage to the air sacs and lining or endothelium of the lung. ARDS' most common symptoms are labored, rapid breathing, nasal flaring, cyanosis blue skin, lips and nails caused by lack of oxygen to the tissues, breathing difficulty, anxiety, stress, tension, joint stiffness, pain and temporarily absent breathing. In some cases ARDS appears to be associated with other diseases, such as acute myelogenous leukemia, with acute tumor lysis syndrome (ATLS) developed after treatment with, e.g., cytosine arabinoside. In general, however, ARDS is associated with traumatic injury, severe blood infections such as sepsis or other systemic illness, high dose radiation therapy, chemotherapy, and inflammatory responses that lead to multiple organ failure, and in many cases death. In premature babies ("premies"), the lungs are not quite developed and, therefore, the fetus is in an anoxic state during development. In addition, lung surfactant, a material critical for normal respiration, is generally not yet present in sufficient amounts at this early stage of life. Premies are therefore susceptible to respiratory problems including bronchoconstriction, lung inflammation and ARDS, among others. When respiratory distress syndrome (RDS) occurs in premies, it is an extremely serious problem. Preterm infants exhibiting RDS are currently treated by ventilation and administration of oxygen and surfactant preparations. When premies survive RDS, they frequently develop bronchopulmonary dysplasia (BPD), also called chronic lung disease of early infancy, which is often fatal.

In another embodiment, the disclosure relates to diagnosis of idiopathic pulmonary fibrosis (IPF). IPF (also known as interstitial lung disease (ILD) or interstitial pulmonary fibrosis), include more than 130 chronic lung disorders that affect the lung by damaging lung tissue, and producing inflammation in the walls of the air sacs in the lung, scarring or fibrosis in the interstitium (or tissue between the air sacs) and stiffening of the lung, thus the name of the disease. Breathlessness during exercise may be one of the first symptoms of these diseases, and a dry cough may be present. Neither the symptoms nor X-rays are often sufficient to tell apart different types of pulmonary fibrosis. Some pulmonary fibrosis patients have known causes and some have unknown or idiopathic causes. The course of this disease is generally unpredictable. Its progression includes thickening and stiffening of the lung tissue, inflammation and difficult breathing. Some people may need oxygen therapy as part of their treatment.

In some embodiments, the disclosure relates to diagnosis of allergic rhinitis (AR) in subjects. Although generally misdiagnosed, allergic rhinitis afflicts one in five Americans and occurs at all ages, thus accounting for an estimated $4 to 10 billion in health care costs each year. Symptoms include nasal congestion, discharge, sneezing, and itching, as well as itchy, watery, swollen eyes. Over time, allergic rhinitis sufferers often develop sinusitis, otitis media with effusion, and nasal polyposis, and may exacerbate asthma. It is associated also with mood and cognitive disturbances, fatigue and irritability. In allergic rhinitis, typically, IgE combines with allergens in the nose to produce chemical mediators, induction of cellular processes, and neurogenic stimulation, causing an underlying inflammation. Degranulation of mast cells results in the release of preformed mediators that interact with various cells, blood vessels, and mucous glands to produce the typical rhinitis symptoms. Most early- and late-phase reactions occur in the nose after allergen exposure. A late-phase reaction, however, is seen in chronic allergic rhinitis, accompanied with hypersecretion and congestion. Repeated exposure causes a hypersensitivity reaction to one or many allergens, and may also produce hyperreactivity to nonspecific triggers such as cold air or strong odors. Non-allergic rhinitis may be induced by infections, such as viruses, or associated with nasal polyps, as occurs in patients with aspirin idiosyncrasy, as well as by pregnancy, hypothyroidism, and exposure to occupational factors or medications. NARES syndrome, a non-allergic type of rhinitis associated with eosinophils in the nasal secretions, typically occurs in middle-aged individuals and is accompanied by loss of smell.

In accordance with the foregoing, the disclosure relates to a non-invasive diagnostic method for diagnosing a pulmonary disease such as asthma, CF, IPF, AR, comprising contacting a sample with the aforementioned articles, systems, and devices.

The "sample" is any biological sample but preferably exhaled breath condensate. Included are EBC fractions, e.g., variable-sized particles or droplets that are aerosolized from the airway lining fluid; water that condenses from gas phase out of the nearly water-saturated exhalate; and water soluble volatiles that are exhaled and absorbed into the condensing breath. In some embodiments, samples include the non-volatile constituents mostly derived from the airway lining fluid particles and in the water-soluble volatile constituents which are found in substantially higher concentrations. In certain embodiments, samples may include bronchoalveolar lavage (BAL) and pleural fluid.

A "subject" to whom the articles, systems, and devices of the disclosure are administered is any air-breathing vertebrate subject, preferably a human, but can be any animal, including a laboratory animal in the context of a trial or screening or activity experiment. Thus, as can be readily appreciated by one of ordinary skill in the art, articles, systems, and devices of the disclosure are particularly suited to administration to any animal, particularly a mammal, and including, but by no means limited to, humans, domestic animals, such as feline or canine subjects, farm animals, such as but not limited to bovine, equine, caprine, ovine, and porcine subjects, wild animals (whether in the wild or in a zoological garden), research animals, such as mice, rats, rabbits, goats, sheep, pigs, dogs, cats, etc.

In one embodiment, the diagnostic method comprises contacting a subject's sample with analytical unit comprising the vehicle chamber 102, auxiliary chamber and the detection chamber; and measuring a parameter associated with a marker. In a specific embodiment, the parameter being measured is a level or amount or concentration of the marker. Particularly, the parameter being measured is the concentration of the peroxide or a derivative thereof in the EBC. In the aforementioned embodiments, the measurement may either be made in situ or ex situ. Preferably, the measurement for the activity, level or concentration of the marker is made in situ. In a second embodiment, the measurement is performed ex situ, e.g., removing the biological sample from the subject's pulmonary organs, e.g., lungs, for analysis in the article or device of the disclosure.

The diagnostic method may comprise determining a level of a reporter signal, e.g., a product of a probe 110 acted upon by the marker. More specifically, the method comprises determining a level of peroxide or a derivative thereof such as peroxide anion ($O_2^{-2}$), or a peroxide radical ($^{\cdot}OH$). As used herein, the term "determining" includes measuring a numerical value of the activity or level of the marker; establishing if the activity or level falls above or below a threshold range; and/or comparing the numerical value of activity or level with a control standard. The control standard may comprise determining a level or activity of the marker in an identical sample (e.g., EBC) obtained from a non-diseased subject, a cured subject or a healthy subject.

In one specific embodiment, the term "determining" comprises measuring the parameter (e.g., activity or level) of at least one pulmonary disease marker selected from hydrogen peroxide or a derivative thereof and optionally a second marker selected from hydrogen ions ($H^+$), malondialdehyde, 8-isoprostanes, thiobarbituric acid reactive substances (TBARS), acetone, nitrosothiols, and nitric oxide-derived products (e.g., NO), or a combination thereof; establishing if said parameter exceeds a first predetermined threshold; and/or comparing the numerical value of parameter with a control standard. The control standard may comprise values for the particular parameter in a sample (e.g., EBC) obtained from a healthy subject. In related embodiments, the term "determining" comprises establishing whether a weighted average (weighted sum) of the parameters associated with a plurality of the aforementioned markers exceeds a predetermined threshold value for said weighted average.

The parameters that are detected generally include an amount or concentration of the marker (e.g., $H_2O_2$) in a sample, e.g., an EBC. Typically, the concentration of an individual analyte is expressed in terms of concentration units, e.g., nmol/L. See, Nagaraja et al. (*Lung India*, 29(2), 123-127, 2012), which states that the $H_2O_2$ concentration is between about 200-2220 nmol/l in smokers and between about 340-760 nmol/L in non-smokers. Alternately, the parameter (e.g., marker levels) may be expressed by taking into consideration a subject's weight (e.g., ng of $H_2O_2$ per kg of body mass). Still further, the parameter may be expressed in absolute amount units, e.g., ng or µg.

In certain embodiments, the parameter may be expressed as a combined amount or activity of a plurality, e.g., 2, 3, 4, 5, 6 or more markers. When used herein, the term "combined amount" or "combined activity" refers to a single numerical value that results from the application of a mathematical function to a plurality of values, for example those amounts obtained for a number of individual markers. Typically, the term "combined amount" or "combined activity" relates to the sum of a group of individual values. A variety of weighting techniques may be employed to arrive at the combined amount or activity, e.g., simple mean, geometric mean, weighted score based on sex of the subject, etc.

When used herein, the term "quantifying" refers to measuring an absolute numerical quantity of a particular marker or probe 110 in a sample, within the margins of experimental error.

In some embodiments, a positive diagnosis is made if the parameter being measured is modulated, e.g., increased or decreased, by at least 5%, at least 10%, at least 15%, at least 20%, at least 25%, at least 30%, at least 40%, at least 50%, at least 60%, at least 70%, at least 80%, at least 90%, at least 1-fold, at least 2-fold, at least 3-fold, at least 4-fold, at least 5-fold, at least 10-fold, at least 50-fold, or more compared to a control. Particularly in the case of oxidative markers, positive diagnosis is made if the level of oxidative marker increases by at least 25%, at least 50%, at least 75%, at least 1-fold, at least 2-fold, at least 3-fold, at least 4-fold, at least 5-fold, at least 10-fold, or more. In some embodiments, the modulation may be expressed in binary terms, e.g., null (or undetectable) versus positive (+) detection. Also, the modulation may be expressed qualitatively (e.g., null, low and high).

In some embodiments, positive diagnosis is made by comparing the determined amount or activity with a predetermined value or range. As used herein, the term "predetermined value or range" refers to a profile or data range that the skilled person would understand is indicative of a particular condition, e.g., a diseased subject. For instance, the predetermined range may be a data range or profile that is typical of a subject suffering from the pulmonary disease, whose outcome was known in the past, e.g., at least 2-fold, at least 3-fold, or a greater fold increase in EBC $H_2O_2$ levels in smokers subject compared to non-smoker subjects.

When used herein, the term "predetermined threshold" refers to a minimum level that the skilled person would determine is indicative of a disease profile based on statistical analysis of levels determined for known pulmonary diseases. For the test to be clinically useful, the threshold should be set at an appropriate level so that non pulmonary diseases with high $H_2O_2$ content in the EBC are properly identified. Increasing the threshold will increase the chance of only certain disease subtypes, e.g., chronic and/or severe forms of pulmonary diseases, being over the threshold.

When used herein, the term "control standard" or "control" refers to a data set or profile that can be used as a reference or comparison in order to define or normalize another data point or set of data. For instance, the term "control" or "control standard" may be data set or profile that is indicative of a particular sub-class of patient, e.g., subjects suffering from chronic asthma. Suitably, the control standard may be a data set or profile indicative of healing or non-healing disease.

Suitably, in other aspects or embodiments of the present disclosure, the "control" or "control standard" can be a data set or profile that can be used as a comparative tool to allow a skilled person to determine whether a disease is likely to be responsive or non-responsive to a treatment, such as, treatment with bronchodilator, steroid and/or anti-inflammatory agents for asthma. In one embodiment, the control standard is a data set or profile indicative of a patient that does not respond well to the treatment. Typically, the control standard is a data set or profile indicative of a patient that responds well to the treatment. Patients that tend to respond well to treatment as disclosed herein exhibit lower combined amount or activity of oxidative markers such as peroxide than patients that tend not to respond well to the treatment.

Embodiments disclosed herein further relate to combined diagnosis and treatment of pulmonary diseases, wherein the diagnostic step is conducted using the compositions, materials, articles, dressings, kits and/or systems described herein. The therapeutic embodiment includes, administering, to a subject having diseased marker profiles (e.g., high peroxide levels in the EBC of an asthma patient), a pharmaceutical agent that is approved for the therapy of the particular disease. Optionally, the method may additionally include determination of whether the subject is responding to the treatment, again, by measuring the disease marker profile in the subject after a period of therapy, e.g., 2 weeks, 1 month, 3 months, 6 months, 1 year, or more.

The skilled person would be able to easily identify whether the pulmonary disease is "responsive to treatment" or not. In particular, the skilled person will readily be able to determine the levels of the markers identified in the present disclosure that are indicative of partial or complete response or poor response to the treatment. The terms "responsive" and "responder(s)" as used herein refer to subjects who experience amelioration of at least 1, 2, 3, 4 or more signs/symptoms associated with the disease. Similarly, "non-responsive" and "non-responder(s)" refers to subjects that are not considered to respond well to treatment, particularly to treatment with the pharmacological agent, e.g., broncho-dilators.

In certain embodiments, a patient may be simultaneously diagnosed and treated with the compositions, articles, systems, or devices described herein. When used herein, the term "simultaneously" means performing the stated objectives, e.g., diagnosis and treatment, together.

In certain embodiments, a patient may be sequentially diagnosed and treated with the articles, systems, or devices described herein. When used herein, the term "sequentially" means the stated objectives, e.g., diagnosis and treatment, are temporally or spatially separated, e.g., diagnosis prior to treatment or diagnosis following treatment or a combination thereof, e.g., $1^{st}$ diagnosis==>treatment==>$2^{nd}$ diagnosis, etc.

Embodiments described herein further enable a caregiver, e.g., a doctor or a nurse, or a patient to determine quickly and reliably whether a pulmonary disease is likely to be non-healing, and to select an appropriate therapy based on this determination. For example, some non-healing pulmonary diseases may necessitate drastic measures, e.g., surgery or lung replacement. Accordingly, embodiments described herein further provide methods of management of a pulmonary disease, e.g., COPD or asthma, comprising determining whether the disease is healing or not (based on marker measurement), followed by applying alternate therapeutic strategies if it is non-healing.

Preferably, the diagnosis and treatment is conducted in situ. Embodiments described herein therefore allow diagnosis and treatment of pulmonary diseases in an easy, non-invasive manner. For instance, the diagnosis may be made in real time and the treatment may be applied to the pulmonary system locally or to the patient (systemically) and the progress of the treatment be monitored over real-time, e.g., dissipation of the oxidative markers in the EBC due to healing.

The methods of the disclosure can be useful for further validating the severity of the pulmonary disease. In one embodiment, the severity of pulmonary diseases is assessed in subjects by measuring an art-appreciated parameter such as FEV1. FEV1 is the maximum amount of air that a subject can forcefully blow out of their lungs in one second and is measured using a spirometer, an instrument that measures pulmonary air flow by having a subject blow into a plastic tube. It is used to show lung capacity and helps pulmonologists classify diseased (e.g., asthmatic or COPD) patients into stages. Thus, the lower the FEV1, the more severe the pulmonary disease. For instance, an FEV1 of 80> of the expected value indicates mild disease; an FEV1 between 50-80 percent indicates moderate disease; an FEV1 between 30-50 percent indicates severe disease; and an FEV1 of <30 percent indicates very severe disease. The FEV1 measurements can be correlated with the marker levels to further validate severity of disease.

In some embodiments, the diagnostic methods of the disclosure perform better than art-appreciated methods. For instance, in patients with intermittent asthma, predicted FEV1% values are normal, but EBC $H_2O_2$ levels are elevated. Thus, the systems and the methods of the present disclosure may be used to supplement and even replace established methods of diagnosis of pulmonary diseases such as asthma.

In some embodiments, disclosed herein is a use of an article as described hereinbefore, e.g., an article comprising (a) a vehicle chamber 102 containing a vehicle 104 for a probe 110; (b) an auxiliary chamber that is physically separated from the vehicle chamber 102 via a first separator 108, wherein the auxiliary chamber contains the probe 110 that is specific to the marker; and (c) a reaction chamber that is physically separated from the vehicle chamber 102 or the auxiliary chamber or both the reaction chamber and the auxiliary chamber via a second separator 122, wherein the reaction chamber contains an surface 124 for the detection of an interaction between the probe 110 and the marker, for the diagnosis of pulmonary diseases, e.g., COPD, IPF, CF, etc.

In another embodiment, disclosed herein is use of an article as described hereinbefore, e.g., an article comprising (a) a vehicle chamber 102 containing a vehicle 104 for a probe 110; (b) an auxiliary chamber that is physically separated from the vehicle chamber 102 via a first separator 108, wherein the auxiliary chamber contains the probe 110 that is specific to the marker; and (c) a reaction chamber that is physically separated from the vehicle chamber 102 or the auxiliary chamber or both the reaction chamber and the auxiliary chamber via a second separator 122, wherein the reaction chamber contains an surface 124 for the detection of an interaction between the probe 110 and the marker, for the manufacture of system or a device for diagnosing pulmonary diseases, e.g., COPD, IPF, CF, etc., in a subject in need thereof.

In another embodiment, disclosed herein are systems or devices comprising the article of the disclosure, for use in diagnosing pulmonary diseases, e.g., COPD, IPF, CF, etc., in a subject.

EXAMPLES

The structures, materials, compositions, and methods described herein are intended to be representative examples of the disclosure, and it will be understood that the scope of the disclosure is not limited by the scope of the examples. Those skilled in the art will recognize that the disclosure may be practiced with variations on the disclosed structures, materials, compositions and methods, and such variations are regarded as within the ambit of the disclosure.

Example 1

Exhaled breath condensate (EBC) collection is a non-invasive method to sample the lungs (Horvath et al. 2005, *Eur Respir J* 26(3):523-48; Kharitonov et al. 2001 *Curr Opin Allergy Clin Immunol* 1(3):217-24; Horvath et al. 2001 *Eur Respir J* 18(2):420-30; Kharitonov and Barnes, 2002 *Markers* 7(1):1-32; Montuschi and Barnes, 2002, *Trends Pharmacol Sci* 23(5):232-7; Barnes et al., 2006, *Am J Respir Crit Care Med* 174(1):6-14). The condensate is obtained by cooling and freezing the exhaled air, which contains significant amounts of water vapor (99% of the volume of the condensate), making the process possible (Horvath et al. 2005 supra; Horvath, 2003, *Eur Respir J* 22(1):187-8; Effros et al., 2002, *Am J Respir Crit Care Med* 165(5):663-9). A small fraction of the condensate is derived from respiratory droplets containing hydrophobic and water soluble molecules (Scheideler et al., 1993, supra). The collection is totally non-invasive and simple using the devices illustrated in the Figures.

In this example, the devices of the disclosure are used to help diagnose asthma in human subjects. For purposes of the study, asthma is defined as patients with a history of three or more episodes of β-2 agonist reversible airway obstruction, who were admitted to a hospital for dyspnea and demonstrated both tachypnea and an inspiratory/expiratory ratio less than 0.5. Smokers, patients with clinical evidence of pneumonia or chronic diseases other than asthma may be excluded. Control subjects comprise healthy hospital staff and patients admitted to the hospital for acute, non-respiratory diseases. The subjects are followed longitudinally with repeated sample collection during and after their hospitalization.

EBC samples 232 are obtained and analyzed from the subjects using a device constructed as illustrated in FIG. 1 and FIG. 2.

As is appreciated in view of the foregoing, the device and method of the disclosure provide a simple, rapid, non-invasive approach for diagnosing and managing treatment of respiratory disease. The device of the present disclosure provides not only the collection of exhaled breath condensate from a subject, but to also test the condensate for chemical properties indicative of asthma (or potentially other diseases) during or immediately following condensate collection. In addition, the device may be configured in detachable parts or cartridges, thus, allowing easy replacement and also maintenance when needed. These features make the device of the present disclosure ideal for home use, as well as for use in a clinic, hospital or emergency room setting.

The exemplified embodiment relates to use of articles, devices, and systems for diagnosing pulmonary diseases such as asthma or COPD. The present aspects and embodiments improve upon existing methods by providing systems and devices that are sensitive, optimized, and non-invasive, which can be used with precision at the point-of-care (POC) for the detection of exhaled breath condensate (EBC) markers associated pulmonary diseases. In particular, the systems and devices disclosed herein comprise components that allow for formulation of active probes 110 that are specific for EBC markers, e.g., by dissolving in a vehicle 104, precisely when needed. The probes 110 contain marker-specific reactive chemicals, which generate active compounds that are capable of reacting with dyes to generate a signal. The setup employed herein is advantageous because in their non-dissolved state, e.g., solid or crystalline form, the analytical probes 110 have a longer shelf life compared to solution-based point-of-care systems. Moreover, partly due to the sensitivity of the reactive chemical to the marker, signals are amplified in a cascade-like effect and detected almost instantaneously (without lag-time). This setup avoids signal decay, which eliminates the need for sophisticated capturing and freezing components that are commonly provided with traditional analytical systems.

Additionally, the devices of the disclosure contain detection units that are adapted for in situ capture and detection of EBC markers. More specifically, the detection units described herein comprise an interaction surface 124, wherein, the vaporous EBC interacts with a probe 110 solution (or suspension), thereby generating a signal, which can be detected in situ with a detector, e.g., a photosensor or photocell, which is optionally integrated into the detection unit. Ideally, the detector and the interaction surface 124 are in close proximity such that any signal generated at the surface 124 is instantaneously processed into a qualitative or a quantitative signal. Depending on the materials used in the housing, the detector may be placed at any suitable location within or in close proximity with the reaction compartment. In some embodiments, the detector is placed along the walls of the article, e.g., reaction chamber. In some embodiments, the detector may be placed in the base of the article, e.g., base of reaction chamber. The detector may comprise components for binary detection (e.g., counter) or more sophisticated means of detection (e.g., integrative detection of a plurality of signals that are separated either in time or in terms of quality).

The devices may be further coupled to a receptacle, wherein, the signal is further processed and readouts are generated to enable a user, e.g., a physician, to diagnose a disease. The receptacle may be equipped with a transmitter, e.g., Bluetooth or wireless transmission, which transmits the readout to a monitor, e.g., a computer or a mobile device such as a smartphone, or the device itself. The Bluetooth connection may also be used to interface with the device to initiate test or run diagnostics and calibrations.

The instant systems and methods can be advantageously employed in the rapid and accurate detection of EBC markers, which are sensitive to heat, light, temperature, moisture and other factors. Discrete units for capturing, cooling and/or processing of EBC, although not required for device functionality, may be included optionally. Accordingly, the systems and devices disclosed herein are specifically adapted for the in situ detection of EBC markers that are indicative of pulmonary diseases such as asthma and COPD. Moreover, the systems disclosed herein can be used in a variety of settings beyond the clinic. For instance, given the compact size and ease of use, the systems and devices disclosed herein may also be self-utilized by patients without the need for constant supervision from healthcare practitioners.

The systems and devices disclosed herein are also advantageous over existing equipment. For instance, the systems disclosed herein are compact and adapted for single-use, which allows them to be employed, accurately, at point-of-care facilities such as outpatient clinics, pathological laboratories, hospitals, etc. To this end, because the system containing the diagnostic unit (e.g., article containing the probe 110, buffer and the reactive chemical) and the analytical unit (e.g., article containing the surface 124 and the detector) can be sold separately from the other components of the system, e.g., as a single-use cartridge, they can be labeled appropriately based on date of manufacture, the type of marker assayed, and/or expected expiration dates, etc. Accordingly, it is expected that use of analytical instruments described herein will not only greatly improve the diagnosis of pulmonary diseases such as asthma, but also permit monitoring and evaluation of the quality of care received by patients. For instance, the devices disclosed herein may be used to monitor whether a patient is responding to a particular drug for treating asthma, or whether a patient is compliant, e.g., with regard to adherence to drug dosages and/or regimen, etc. The systems and devices described herein may also be used in the titration, dosing, and/or personalization of the therapeutic drugs.

Example 2

A prototype of the device was created in accordance with the present disclosure.

In order to test the device, first, the effects of outside light interference were examined by measuring a "blank." This can be measured by taking a measurement in ambient light with an empty testing chamber. The blank sets a baseline for the background noise from the sensor and can be used to identify errors caused by the sensor when the background noise is significantly different from what is expected. Performing a blank test before testing any samples also ensures the device is working correctly without wasting resources. Occasionally, a very high light reading is recorded that indicates the sensor has reached the maximum reading. The maximum (max) reading is the result of a small amount of ambient light getting into the testing chamber when the sensor starts recording before the lid can be fully closed. Baselining is not a requirement; and is purely an optional feature that can be used to identify errors in operation or damaged devices.

To accurately estimate the peroxide content of an unknown sample, a calibration curve was created by testing a set of known peroxide concentrations. A 5-point calibration curve was selected because it provides a high degree of certainty when estimating concentrations.

Figure 8:
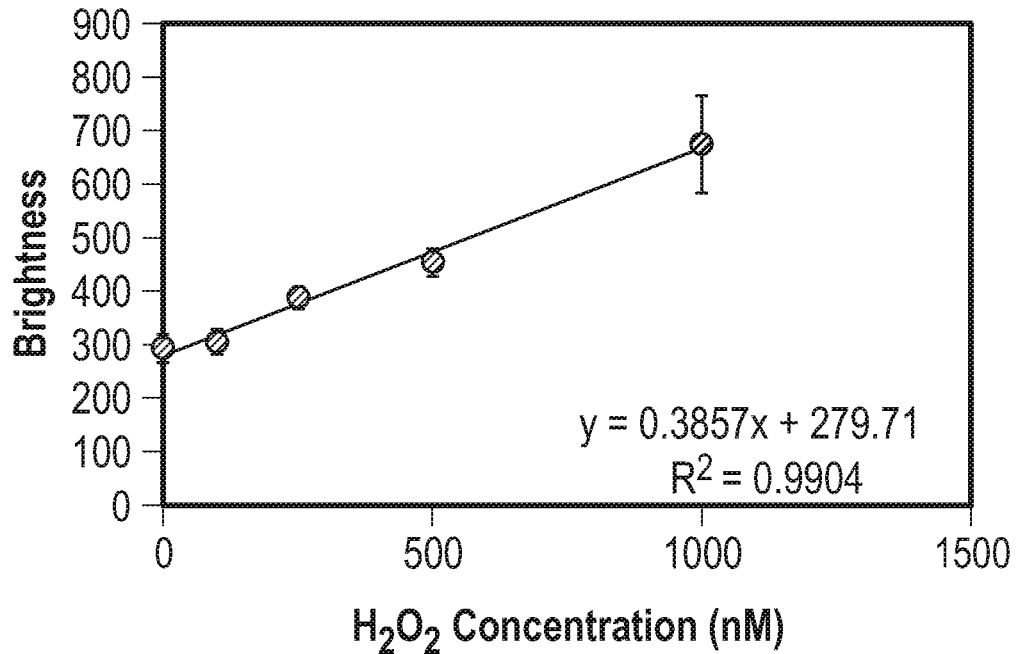
FIG. 8 shows exemplary results of experiments on measurement of $H_2O_2$ using the devices of the disclosure. The data show that the signal (brightness) increases linearly with increasing concentrations of $H_2O_2$ at all values tested (range: 0 μM to 1 μM).

Gradient hydrogen peroxide ($H_2O_2$) solutions were created from stock. $H_2O_2$ was diluted in deionized water to reach the desired concentration. The exception is the 0 nM concentration which is composed entirely of deionized water (FIG. 8 shows measurements with de-ionized water). Each $H_2O_2$ solution is tested three times to measure variance. The "brightness" value of each solution can be calculated in two ways. The first method we used was to measure the area under the curve by integrating each measurement, or taking the sum of every measurement made (with the exception of maxed out measurements). The current method is to take an average of all the measurements taken in a reading and assigning that number as the brightness value. Both methods work equally well, but the average method was used due to its simplicity. A time of 30 seconds was established because the end of the light emission produced by the reaction can be observed for most concentrations. A shorter time frame may be used as long as all samples are tested with an identical time frame. The shortest time frame used successfully was a single instant measurement.

Figure 9:
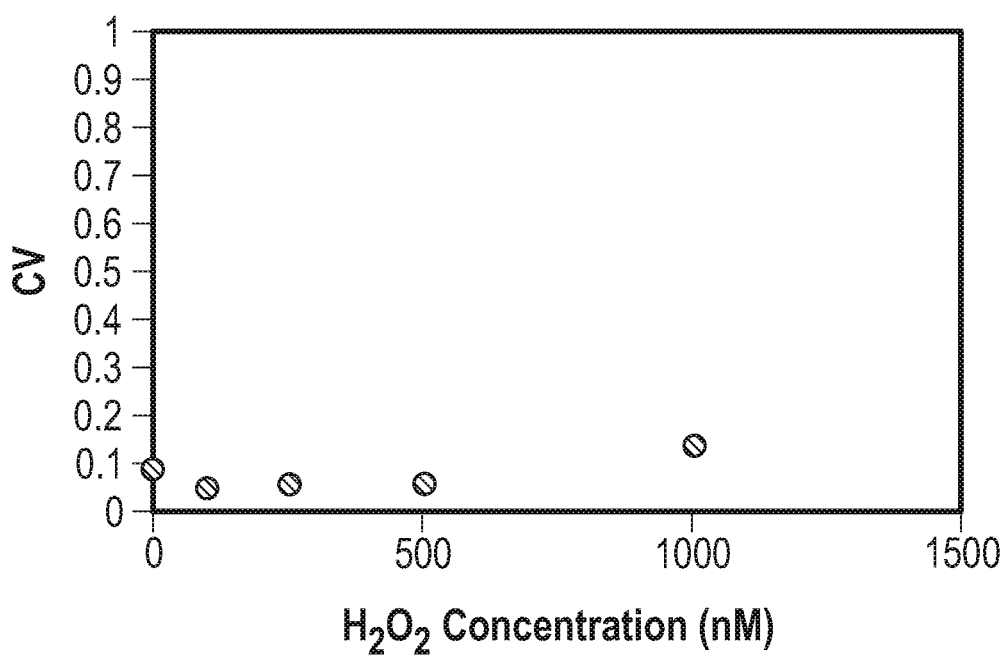
FIG. 9 shows coefficient of variance (CV) associated with the measurements of $H_2O_2$ using the devices of the disclosure (n=3). The data show that the signal generated was highly reproducible across triplicates.

Once all of the samples in the calibration have been tested, the brightness values were plotted on a graph and an equation is created to best fit the line. An $R^2$ value (correlation) was calculated based on the equation as a measure of the reliability of the line to accurately estimate unknown $H_2O_2$ content. A value of 1 would represent a perfect line. The equation is also used to estimate peroxide contents by using the brightness value as the y variable and solving for the x variable. A limit of detection is calculated by dividing 3 times the standard deviation of the OM concentration by the slope of the graph. A coefficient of variance (CV) is calculated by dividing the standard deviation of a sample by the brightness value to get a measure of error in each set of three samples. An average CV is calculated by averaging the CVs from the calibration set and used to estimate an overall error rate for the assay. The plot of CVs is used to identify particularly error prone peroxide samples and possible mistakes in mixing each concentration. Results are shown in FIG. 8 and FIG. 9.

As can be seen from FIG. 8, the signal (brightness) that is generated by the device increases proportionately with increasing concentrations of $H_2O_2$. The correlation coefficient ($R^2$) value of 0.99 demonstrates a statistically significant correlation between the two parameters. The data show that the device can accurately detect $H_2O_2$ concentrations between 0 nM and 1 µM. Furthermore, as demonstrated by the data in FIG. 9, there was little variance between individual measurements. The coefficient of variance (CV) values of about 0.1 or less demonstrates the superior reliability of the readouts that are generated by the device. Even at the highest tested concentration (1 µM), the CV values are within acceptable levels for biosensor equipment. The data show that the device can accurately detect $H_2O_2$ concentrations between 0 nM and 1 µM with high degree of reproducibility and reliability.

While a number of exemplary aspects and embodiments have been discussed above, those skilled in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

Throughout this disclosure, various patents, patent applications and publications are referenced. The disclosures of these patents, patent applications, accessioned information (e.g., as identified by PUBMED accession numbers) and publications in their entireties are incorporated into this disclosure by reference in order to more fully describe the state of the art as known to those skilled therein as of the date of this disclosure. This disclosure will govern in the instance that there is any inconsistency between the patents, patent applications and publications cited and this disclosure.

We claim:

1. An article for measuring a disease marker in exhaled breath condensate (EBC) comprising,
   (a) a vehicle chamber containing a vehicle for a probe;
   (b) an auxiliary chamber that is physically separated from the vehicle chamber via a first separator, wherein the auxiliary chamber contains the probe that is specific to the marker;
   (c) a reaction chamber that is physically separated from the vehicle chamber or the auxiliary chamber or both the reaction chamber and the auxiliary chamber via a second separator, wherein the reaction chamber contains an surface for detection of the interaction between the probe and the marker; and
   (d) a detector for detecting a signal issued from said reaction chamber.

2. The article of claim 1, wherein the marker is hydrogen peroxide ($H_2O_2$) or a derivative thereof selected from peroxide anion ($O_2^{-2}$), or a peroxide radical (*OH).

3. The article of claim 1, wherein the probe comprises a marker-reactive chemical and a dye.

4. The article of claim 3, wherein the dye is activated by a product of the reaction between the marker and the marker-reactive chemical.

5. The article of claim 4, wherein the dye is activated in situ.

6. The article of claim 1, wherein the marker is $H_2O_2$ and the probe comprises $H_2O_2$-reactive chemical and a dye.

7. The article of claim 6, wherein the reactive chemical is bis(2,4,6-trichlorophenyl) oxalate, bis(2-carbopentyloxy-3,5,6-trichlorophenyl)oxalate, oxalic acid bis[2,4,5-trichloro-6-(pentyloxycarbonyl)phenyl]ester, bis(2-itrophenyl) oxalate, bis(2,4-dinitrophenyl) oxalate, bis(2,6-dichloro-4-nitrophenyl) oxalate, bis(2,4,6-trichlorophenyl) oxalate, bis(3-trifluoromethyl-4-nitrophenyl) oxalate, bis(2-methyl 4,6-dinitrophenyl) oxalate, bis(1,2-dimethyl-4, 6-dinitrophenyl) oxalate, bis(2,4-dichlorophenyl) oxalate, bis(2,5-dinitrophenyl) oxalate, bis(2-formyl-4-nitrophenyl) oxalate, bis(pentachlorophenyl) oxalate, bis(pentalluorophenyl) oxalate, bis(1,2-dihydro-2-oxo-1-pyridyl) glyoxal, bis-N-phthalmidyl oxalate, bis(2,4,5 trichloro-6-carbopentoxyphenyl) oxalate, bis(2,4,5-trichloro-6-carbobutoxyphenyl) oxalate, bis(2,4,6-trichlorophenyl) oxalate, or phthalimido 3,6,6-trisulfo-2-naphthyloxalate.

8. The article of claim 6, wherein the dye is selected from iptycene compounds, anthracenes, diphenylanthracenes, 9,10-bis(phenylethynyl) anthracene, benzanthracenes, phenanthrenes, naphthacenes, pentacenes, poly(arylene)s, poly(phenylene vinylene)s, poly(phenylene ethynylene)s, 5-amino-2,3-dihydrophthalazine-1,4-dione, 3-aminophthalhydrazide, 2,4,5-triphenylimidazole, 10, 10'-dialkyl-9,9'-biacridinium salts, and 9-chlorocarbonyl-10-methylacridinium chloride.

9. The article of claim 1, wherein said vehicle is an organic solvent selected from the group consisting of: ethylene glycol ethers, diethyl ether, diamyl ether, diphenyl ether, anisole, tetrahydrofuran, dioxane, ethyl acetate, acetone, acetonitrile, propyl formate, amyl acetate, dimethyl phthalate, diethyl phthalate, dibutyl phthalate, dioctyl phthalate, methyl formate, triacetin, diethyl oxalate, dioctyl terphthalate, citric acid ester, methyl benzoate, ethyl benzoate, butyl benzoate, benzene, ethyl benzene, butyl benzene, toluene, xylene, chlorobenzene, o-dichlorobenzene, m-dichlorobenzene, chloroform, carbon tetrachloride, hexachloroethylene, tetrachlorotetrafluoropropane, or combinations thereof.

10. The article of claim 1, wherein the probe further comprises a catalyst.

11. The article of claim 1, wherein the catalyst is imidazole.

12. The article of claim 1, wherein the marker comprises a plurality of markers comprising a first marker which is hydrogen peroxide or a derivative thereof and optionally a second marker selected from hydrogen ions ($H^+$), malondialdehyde, 8-isoprostanes, thiobarbituric acid reactive substances (TBARS), acetone, nitrosothiols, and nitric oxide-derived products.

13. The article of claim 1, wherein a plurality of dyes, each which is specific for the disease marker, are employed.

14. The article of claim 1, wherein the auxiliary chamber is located inside the vehicle chamber or append-able thereto.

15. The article of claim 1, wherein the first separator comprises a foil, a plastic or a valve.

16. The article of claim 1, wherein the first separator is removed via mechanical force, physical force, or manually.

17. The article of claim 16, wherein the first separator is removed via a mechanical force comprising twisting.

18. The article of claim 16, wherein when the first separator is removed, the vehicle contained in the vehicle chamber enters the reaction chamber and mixes with the probe contained in the reaction chamber.

19. The article of claim 18, wherein the mixing comprises dissolution of the probe in the vehicle.

20. The article of claim 1, wherein the reaction chamber is contained in the vehicle chamber or append-able thereto.

21. The article of claim 20, wherein the reaction chamber is physically separated from the auxiliary chamber via the second separator.

22. The article of claim 21, wherein the second separator comprises a foil, a plastic or a valve.

23. The article of claim 1, wherein the reaction chamber further comprises an elongated member that is positioned opposite to the second separator.

24. The article of claim 23, wherein the elongated member is a pin, nail, needle, rod, or plastic tip that penetrates the second separator via mechanical force or physical force.

25. The article of claim 1, wherein the surface for detecting the interaction between the probe and the marker comprises an adsorptive material.

26. The article of claim 25, wherein the surface comprises a chemisorptive or a physisorptive material.

27. The article of claim 25, wherein the surface comprises a sponge, charcoal, activated carbon, cellulose, lignin, polycaprolactone (PCL) or a combination thereof.

28. The article of claim 1, wherein the reaction chamber further comprises a chip.

29. The article of claim 28, wherein the chip is a microfluidic chip.

30. The article of claim 1, wherein the reaction chamber further comprises a thin transparent or translucent window that is pervious to a signal generated by the interaction between the probe and the marker.

31. The article of claim 30, wherein the window comprises glass or plastic.

32. The article of claim 1, further comprising a collection unit for collecting EBC, wherein the collection unit comprises a first end that is attachable to the article and a second end that contains a breathing inlet.

33. The article of claim 32, wherein the first end of the collection unit is attachable to the reaction chamber or an end in the article that is proximate to the reaction chamber.

34. The article of claim 32, wherein the first end in the collection unit comprises a mesh that is pervious to gas but semi-pervious or impervious to liquid.

35. The article of claim 32, wherein the collection unit is T-shaped, L-shaped or S-Shaped.

36. The article of claim 32, wherein the collection unit further comprises a plunger at the first end that is attachable to the article.

37. The article of claim 32, further comprising a receptacle for analytically measuring a signal generated by the probe-marker interaction.

38. The article of claim 1, further comprising a receptacle for analytically measuring a signal generated by the probe-marker interaction.

39. The article of claim 37, wherein the receptacle comprises a detector for detecting a signal.

40. The article of claim 39, wherein the signal is a chemiluminescent, a fluorescent or a phosphorescent signal.

41. The article of claim 1, wherein the detector is positioned either on the side wall of the reaction chamber, or on the bottom.

42. The article of claim 1, wherein the detector comprises a sensor which takes a measurement by integrating the signal picked up by the sensor over a defined period of time.

43. A kit comprising, in one or more packages,
(1) the article of claim 1, wherein components (a), (b) and (c) are present separately or as a unit; and
(2) instructions for using the kit.

44. A method for measuring the in situ detection of a disease marker in a subject's exhaled breath condensate (EBC), comprising,
(a) activating the article of claim 1 by disengaging the first separator to allow mixing between the vehicle and the probe;
(b) contacting a sample comprising the EBC with the equipped article of (a) to facilitate an interaction between the probe and the marker;
(c) detecting a signal generated from the interaction between the probe and the marker.

45. The method of claim 44, wherein the signal is a chemiluminescent or fluorescent signal.

46. The method of claim 44, wherein the EBC comprises a plurality of markers comprising a first marker which is hydrogen peroxide or a derivative thereof and optionally a second marker selected from hydrogen ions (H+), malondialdehyde, 8-isoprostanes, thiobarbituric acid reactive substances (TBARS), acetone, nitrosothiols, and nitric oxide-derived products.

47. A method of diagnosing a pulmonary disease in a subject in need thereof, comprising the steps of:
activating the article of claim 1 by mixing the vehicle with the probe;
contacting the subject's exhaled breath condensate (EBC) sample with the activated article for a period sufficient to permit interaction between the probe and a pulmonary disease marker present in the EBC; and
detecting a signal generated from the interaction between the probe and the marker.

48. The method of claim 47, wherein the pulmonary disease is asthma, chronic obstructive pulmonary disease (COPD), idiopathic pulmonary disease (IPF), acute respiratory distress syndrome (ARDS), or a combination thereof.

49. The method of claim 47, wherein the marker comprises a plurality of markers comprising a first marker which is hydrogen peroxide or a derivative thereof and optionally a second marker selected from hydrogen ions (H+), malondialdehyde, 8-isoprostanes, thiobarbituric acid reactive substances (TBARS), acetone, nitrosothiols, and nitric oxide-derived products.

50. A method for the combined diagnosis and treatment of a pulmonary disease in a subject, comprising,
activating the article of claim 1 by removing the first separator to allow the vehicle and the probe to mix;
contacting a first exhaled breath condensate (EBC) sample obtained from the subject with the activated article, thereby generating a first signal;
contacting a second EBC sample from a healthy subject (control) with an identically activated article of claim 1, thereby generating a second signal;
detecting a parameter which is signal intensity or signal strength from both first and second signals;
correlating the parameter with the marker levels or activities;
determining that the subject is suffering from the pulmonary disease if the first parameter is modulated compared to the second parameter; and
administering a therapeutic composition to subjects who are determined to suffer from the pulmonary disease.

51. The method of claim 50, wherein
the pulmonary disease is asthma, COPD or IPF;
the marker is hydrogen peroxide or a derivative thereof selected from peroxide anion ($O_2^{-2}$), or a peroxide radical (*OH);
the subject is determined to suffer from the pulmonary disease if the level of hydrogen peroxide or a derivative thereof is elevated in the first sample from the subject compared to the level of hydrogen peroxide or a derivative thereof in the second sample from healthy subjects (control); and
a therapeutic composition for the treatment of the pulmonary disease is administered to the subjects who have been determined to suffer from the pulmonary disease.

52. A system for measuring a disease marker in exhaled breath condensate (EBC) comprising,
(I) an article comprising,
(a) a vehicle chamber containing a vehicle for a probe for the detection of the marker;
(b) an auxiliary chamber that is physically separated from the vehicle chamber via a first separator, wherein the auxiliary chamber contains the probe that is specific to the marker; and
(c) a reaction chamber that is physically separated from the vehicle chamber or the auxiliary chamber or both the reaction chamber and the auxiliary chamber via a second separator, wherein the reaction chamber contains an surface for detection of the interaction between the probe and the marker;
(II) a collection unit comprising a first end that is attachable to the article and a second end that contains a breathing inlet;
and;
(III) a receptacle for analytically measuring a signal generated by the probe-marker interaction.

53. A kit comprising, in one or more packages,
(1) the system of claim 52, wherein each subcomponent 1(a), 1(b) and 1(c) or component (I), (II) and (III) are provided separately or as a unit; and
(2) instructions for using the kit.

* * * * *